United States Patent
Wolleb et al.

(10) Patent No.: US 6,790,593 B2
(45) Date of Patent: Sep. 14, 2004

(54) METALLOCENYL-PHTHALOCYANINES

(75) Inventors: Heinz Wolleb, Fehren (CH); Annemarie Wolleb, Fehren (CH); Beat Schmidhalter, Bubendorf (CH); Jean-Luc Budry, Riehen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/037,106

(22) Filed: Oct. 22, 2001

(65) Prior Publication Data

US 2002/0099204 A1 Jul. 25, 2002

Related U.S. Application Data

(62) Division of application No. 09/365,471, filed on Aug. 2, 1999, now Pat. No. 6,399,768.

(30) Foreign Application Priority Data

Aug. 11, 1998 (CH) .............................................. 1653/98

(51) Int. Cl.$^7$ ................................................. G11B 7/24
(52) U.S. Cl. .......................... 430/270.16; 430/1; 430/2; 430/945; 428/648
(58) Field of Search ............................ 430/270.16, 945, 430/1, 2; 540/140, 139; 556/143; 428/64.8

(56) References Cited

U.S. PATENT DOCUMENTS

| | | | | |
|---|---|---|---|---|
| 5,124,067 A | 6/1992 | Itoh et al. | ............... | 252/299.2 |
| 5,292,615 A | 3/1994 | Yamada et al. | ............ | 435/270 |
| 5,594,128 A | 1/1997 | Wolleb | ...................... | 540/122 |
| 6,399,768 B1 * | 6/2002 | Wolleb et al. | .............. | 540/140 |

FOREIGN PATENT DOCUMENTS

| | | |
|---|---|---|
| DE | 41 12 402 | 4/1992 |
| EP | 0373643 | 6/1990 |
| EP | 0 511 598 | 11/1992 |
| EP | 0 600 427 | 6/1994 |
| EP | 0811506 | 12/1997 |
| JP | 8-118800 | 5/1996 |
| WO | 97/23354 | 7/1997 |

OTHER PUBLICATIONS

J. Organomet. Chem. 468 (1–2) (1994) pp. 205–212.
Chin. Chem. Lett. 4(4) (1993) pp. 339–342.
New J. Chem. 21 (2)(1997) pp. 267–271.
J. Organomet. Chem. 541 (1–2) (1997) pp. 441–443.
J. Chem. Soc. Chem. Commun. 1995, pp. 1715–1716.
Inorg. Chem 37(1998) pp. 411–417.
Chem. Abst. 121:69195b p. 883, (1994).
Chem. Abst. 126:287109w p. 1465, (1997).
Chem. Abst. 128:83592e p. 1307, (1998).
Tetrahedron Letters, 40 (1999), pp. 3263–3266.
Chem. Abst. 131:222490, (1999).
Chem. Abst. 119:285025x p. 1040, (1993).
Abstract for EP 0373643 (1990).
Poon et al., Organometallics, vol. 18, (1999), pp. 3528–3533.

* cited by examiner

*Primary Examiner*—Martin Angebranndt
(74) *Attorney, Agent, or Firm*—Kevin T. Mansfield

(57) ABSTRACT

There was found a metallocenyl-phthalocyanine or its metal complex of a divalent metal, oxometal, halogenometal or hydroxymetal, in which at least one of the four phenyl rings of the phthalocyanine contains, bound via a bridge unit E, at least one metallocene radical as substituent, E being composed of a chain of at least two atoms or atom groups selected from the group consisting of —$CH_2$—, —C(=O)—, —CH($C_1$-$C_4$alkyl)—, —C($C_1$-$C_4$alkyl)$_2$—, —NH—, —S—, —O— and —CH=CH—, as well as mixtures of the novel compounds which comprise, inter alia, isomers, a process for the production, the use and recording media comprising the novel compounds.

16 Claims, No Drawings

METALLOCENYL-PHTHALOCYANINES

This is a divisional of application Ser. No. 09/365,471, filed on Aug. 2, 1999, now U.S. Pat. No. 6,399,768 B1.

The present invention relates to novel metallocenyl-phthalocyanines, to a process for their preparation and to their use.

The field of this invention is that of the optical recording of information for writable recording media, the information being recorded via different optical properties of a dye on written and unwritten places. Corresponding recording media are known, for example, under the name "WORM" systems (write once read many) and are further categorised into e.g. "CD-R" or "DVD-R".

The use of dyes which absorb radiation in the near infrared range (NIR range) for recording information in WORM systems is described, inter alia, by M. Emmelius in Angewandte Chemie, No. 11, pages 1475–1502 (1989). By irradiating such recording materials with laser it is possible to achieve the change in absorption required for recording information in binary form via physical changes (for example by sublimation or diffusion) or via chemical changes (for example photochromism, isomerisations or thermal decomposition of the dye).

Substituted phthalocyanines are an important class of dyes for use in such WORM systems because they have high NIR absorptions in the range from 700 nm to 900 nm when correspondingly substituted and dependent on the central atom which is usually present.

The most stringent requirements are placed on the recording layer to be used, such as high refractive index, high initial reflectivity, narrow absorption bands in the solid state, uniformity of the writing width at different pulse duration, high light stability in daylight as well as under weak laser radiation (readout) coupled with high sensitivity to intense laser radiation (inscribing), low noise, high resolution as well as, most importantly, very little statistical jitter of the pits over a desired value at optimum writing performance.

As the recording layer is normally applied from a solution, typically by spin-coating, the dyes should also be readily soluble in conventional solvents, which are described, inter alia, in EP-A 511 598 (independently from the distinction made therein between polar and nonpolar solvent).

Phthalocyanine compounds containing at least one ferrocene unit as substituent are known. J. Organomet. Chem. 468(1–2) (1994), for example, describes 205–212 1, 1", 1"", 1""''-(29H, 31H-phthalocyanine-2,9,16,23-tetrayl)tetrakis-ferrocene; Quin. Chem. Lett. 4(4) (1993) 339–342 describes [1-(11-ferrocenylundecyl)-1'-[4-[4-[[9,16,23-tris(2,2-dimethylpropoxy)-29H,31H-phthalocyanine-2-yl]oxy]phenoxy]butyl]-4,4'-bipyridiniumato(2-)-$N^{29},N^{30},N^{31},N^{32}$]-zinc dibromide; New J. Chem. 21(2) (1997) 267–271 describes 1,1"-[[9,23-bis(dodecylthio)-29H,31H-phthalocyanine-2,16-diyl]bis(nitrilomethylidine)] bisferrocene; and J. Organomet. Chem. 541(1–2) (1997) 441–443 describes the synthesis of [Cp(dppe)Fe—CN—MnPc]$_2$O (with dppe=1,2-ethanediylbis (diphenylphosphine); Cp=cyclopentadienyl; Pc=phthalocyanine).

J.Chem.Soc., Chem.Commun. 1995, 1715–1716 describes the preparation of liquid crystalline ferrocenyl-phthalocyanines, ferrocenecarbonyl chloride being reacted with a hydroxy group-substituted and metal-free phthalocyanine to the corresponding ester compound.

Inorg. Chem. 37 (1998) 411–417 describes the synthesis of bis(ferrocenecarboxylato)-(phthalocyaninato)silicium, the ferrocene unit being bound to the central atom.

WO-A 9723354 describes optical recording materials based on phthalocyanines which contain as substituents inter alia ferrocene units bound to the central atom.

The use of CD-R as archiving and back-up media for computer data increasingly requires faster writing speeds. In contrast, use as audio medium requires slower (1×) speeds. Accordingly, the recording layers continuously need to be optimised for such a wide-band behaviour (at present 1×–8×), which places extraordinarily high requirements on the recording layers to be used. It is known that recording layers containing phthalocyanines show very good measurement values for high speeds (2×–6×) but less favourable 1×-values for the length deviation of the pits and lands from the norm, and also for the jitter. Jitter is in effect understood to be a time error at the change of a signal as a result of a pit or a marked range being too short or too long. On a CD-R, for example, the length of the pits can vary between 3T and 11T (1T=231.4 ns). If, for example, the length of a 3T pit is even marginally fallen short of or exceeded, then this may result in an increased number of BLERs (=block error rate, designating the number of physical errors on the CD) and thus in a loss in quality. The error rate (BLER) should as a rule be less than 220 per second.

Different proposals have been made to solve the cited difficulties when using phthalocyanines; in particular attempts were made to lower the decomposition temperature which is higher than that of other dye classes, especially cyanines.

DE-A 4 112 402, for example, proposes to use as recording film a mixture consisting of a phthalocyanine and a cyanine (as light absorber element) which absorbs in the cited wave-length range. However, also in this instance does repeated readout result in the destruction of the light absorber so that the desired properties are not obtained. It is moreover known that cyanine dyes are not lightfast and that it is therefore usually necessary to add a stabiliser.

EP-A 600 427 describes an optical recording medium, the recording layer of which comprises a phthalocyanine and an additive, e.g. a ferrocene derivative, a metal acetylacetonate or an antiknock additive. According to that application, the addition of the cited additives improves the quality of the recording. Disadvantages are, however, the use of an additional substance in the form of an additive and the difficulties in the recovery of the dye which is obtained in the production of the recording layer because, to use the dye again, the additive must either be removed or its amount must be readjusted.

JP-A 8-118800 describes optical recording media, the recording layer of which comprises an azo compound which is substituted by a ferrocene unit. Furthermore, mixtures of these azo compounds with, inter alia, phthalocyanines and pentamethinecyanines are described. The disadvantage in this case is that neither the azo compound nor the phthalocyanines can be used by themselves to give a satisfactory recording layer.

Accordingly, it is the object of this invention to provide additional phthalocyanines which are substituted by metallocene units and to provide improved recording materials based on phthalocyanines for the production of, and for use in, optical recording media. In particular, the metallocenyl-phthalocyanines used as recording materials in optical information recording media, preferably in CD-R, shall fulfill the desired wide-band behaviour (1×8×) and shall have excellent recording and reproduction characteristics in the wavelength of a semiconductor laser (770–790 nm).

In addition, preferred jitter values in the range of ±35 ns and length deviations in the ranges of ±40 ns (T3 pits/lands) and ±60 ns (T11 pits/lands) shall be maintained.

Furthermore, an improved process for the recovery of the dye used in the production of the recording layer shall be found. It should moreover be possible to use the metallocenyl-phthalocyanines by themselves, i.e. without additional additives, as recording materials.

Accordingly, a metallocenyl-phthalocyanine or its metal complex of a divalent metal, oxometal, halogenometal or hydroxymetal has been found in which at least one of the four phenyl rings of the phthalocyanines contains, bound via a bridge unit E, at least one metallocene radical as substituent, E being composed of a chain of at least two atoms or atom groups selected from the group consisting of —$CH_2$—, —C(=O)—, —CH($C_1$–$C_4$alkyl)—, —C($C_1$–$C_4$alkyl)$_2$—, —NH—, —S—, —O— and —CH=CH—.

In addition there have been found mixtures of the novel compounds which comprise, inter alia, isomers, as well as a process for their preparation, their use and the optical recording media comprising the novel compounds.

A preferred embodiment of this invention relates to metallocenyl-phthalocyanines of formula I

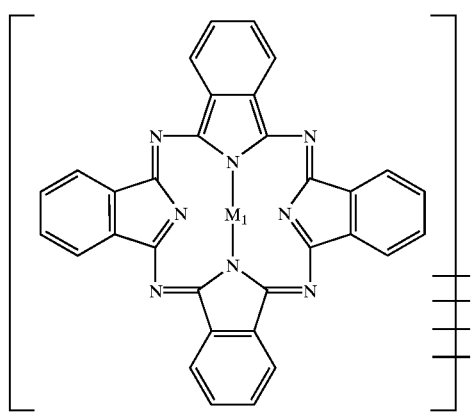

(I)

wherein $M_1$ is a divalent metal, an oxometal group, halogenometal group or hydroxymetal group, or two hydrogen atoms, X is halogen, such as chloro, bromo or iodo, preferably chloro or bromo, particularly preferably bromo, $Y_1$ is —$OR_1$, —OOC—$R_2$, —$NHR_1$, —$N(R_1)R_2$, preferably —$OR_1$, $Y_2$ is —$SR_1$, $R_3$ is

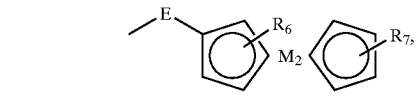

$R_3$ is preferably:

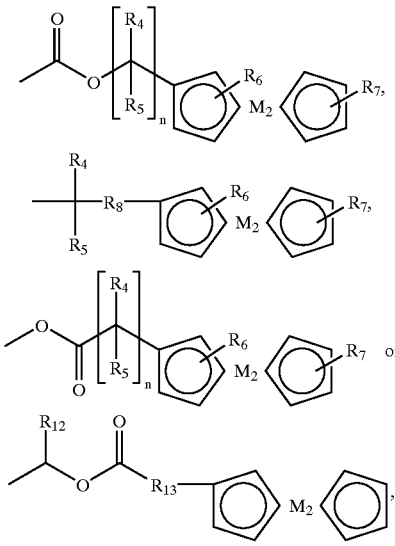

wherein $R_4$ and $R_5$ may be each independently of the other hydrogen or $C_1$–$C_4$alkyl, n may be a number from 1 to 4, $R_6$ and $R_7$ are each independently of the other hydrogen, halogen, such as fluoro, chloro, bromo or iodo, $C_1$–$C_4$alkyl, $C_1$–$C_4$alkoxy, amino-$C_1$–$C_4$alkyl, diarylphosphine, or phosphorus-containing $C_1$–$C_4$alkyl, such as —$CH_2$—$PAr_2$ or —CH(Me)—$PAr_2$, Ar being unsubstituted or substituted phenyl, $R_8$ may be —O—$R_9$—, —C(=O)—O—$R_9$ or —O—C(=O)—$R_9$—, wherein $R_9$ may be a single bond, $C_1$–$C_4$alkylene or $C_2$–$C_4$alkenylene, and $M_2$ is a divalent transition metal, and wherein $R_{12}$ is hydrogen or methyl, $R_{13}$ is a single bond, —$CH_2$—, —$CH_2CH_2$—, —CH=CH—, —$CH_2$—C(=O)— or —$CH_2CH_2$—C(=O)—, x may be a rational number from 0 to 8, preferably from 0 to 5, particularly preferably from 0 to 3, $y_1$ and $y_2$ may be each independently of the other a rational number from 0 to 6, $y_1$ preferably being an integer from 1 to 6, particularly preferably from 3 to 5, especially preferably from 4, and $y_2$ preferably being a rational number from 0 to 2.0, z may be a number from 1 to 4, preferably from 1 to 3, particularly preferably from 1 to 2, and wherein ($x+y_1+y_2+z$) is ≦16, wherein $R_1$ and $R_2$ may be each independently of the other $C_1$–$C_{20}$alkyl which is unsubstituted or substituted by halogen, hydroxy, $C_1$–$C_{20}$alkoxy, $C_1$–$C_{20}$alkylamino or $C_2$–$C_{20}$dialkylamino and which may be interrupted by —O—, —S—, —NH— or —$NR_{10}$—, wherein $R_{10}$ may be $C_1$–$C_6$alkyl, $C_5$–$C_{20}$cycloalkyl, $C_2$–$C_{20}$alkenyl, $C_5$–$C_{12}$cycloalkenyl, $C_2$–$C_{20}$alkynyl, $C_6$–$C_{18}$aryl or $C_7$–$C_{18}$aralkyl, and wherein one or two ligands may optionally be bound to the divalent metal atom, the oxometal group, halogenometal group or hydroxymetal group.

The substituents X, Y$_1$, Y$_2$ and R$_3$ are preferably at the benzene nuclei of the metallocenyl-phthalocyanine I.

The divalent metal used may be divalent transition metal cations, in particular of copper, zinc, nickel, palladium, platinum, manganese or cobalt, preferably of palladium or copper.

The oxometal group used may be VO, MnO or TiO.

The halogenometal group used may be Al—Cl, Al—Br, Al—F, Al—I, Ga—Cl, Ga—F, Ga—I, Ga—Br, In—Cl, In—F, In—I, In—Br, Tl—Cl, Tl—F, Tl—I, Tl—Br, FeCl, or RuCl and also CrCl$_2$, SiCl$_2$, SiBr$_2$, SiF$_2$, SiI$_2$, ZrCl$_2$, GeCl$_2$, GeBr$_2$, GeI$_2$, GeF$_2$, SnCl$_2$, SnBr$_2$, SnI$_2$, SnF$_2$, TiCl$_2$, TiF$_2$, TiBr$_2$.

The hydroxymetal group may be MnOH, Si(OH)$_2$, Ge(OH)$_2$, Zr(OH)$_2$, Mn(OH)$_2$, AlOH or Sn(OH)$_2$.

$C_1$–$C_{20}$Alkyl is, for example, methyl, ethyl, n-, i-propyl, n-, sec-, i-, tert-butyl, n-, neopentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, preferably $C_1$–$C_{12}$alkyl, such as methyl, ethyl, n-, i-propyl, n-, sec-, i-, tert-butyl, n-, neopentyl, hexyl, heptyl, octyl, nonyl, decyl, undecyl, dodecyl and, in particular, branched $C_3$–$C_{12}$alkyl such as i-propyl, sec-, i-, tert-butyl, neopentyl, 1,2-dimethylpropyl, 1,3-dimethylbutyl, 1-isopropyl-propyl, 1,2-dimethylbutyl, 1,4-dimethylpentyl, 2-methyl-1-iso-propylpropyl, 1-ethyl-3-methylbutyl, 3-methyl-1-isopropylbutyl, 2-methyl-1-isopropylbutyl, or 1-tert-butyl-2-methylpropyl, and $C_1$–$C_6$alkyl such as methyl, ethyl, n-, i-propyl, n-, sec-, i-, tert-butyl, n-, neopentyl, n-hexyl, 2,2-dimethylhexyl, particularly preferably $C_1$–$C_4$-alkyl such as methyl, ethyl, n-, i-propyl, n-, sec-, i-, tert-butyl and 2,4-dimethyl-3-pentyl. $C_5$–$C_{20}$Cycloalkyl is, for example, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, preferably $C_5$–$C_8$-cycloalkyl such as cyclopentyl, cyclohexyl, cycloheptyl, cyclooctyl.

$C_2$–$C_{20}$Alkenyl is, for example, ethenyl, n-, i-propenyl, n-, sec-, i-, tert-butenyl, n-, neopentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, preferably $C_2$–$C_6$alkenyl such as ethenyl, n-, i-propenyl, n-, sec-, i-, tert-butenyl, n-, neopentenyl, n-hexenyl, particularly preferably $C_2$–$C_4$alkenyl such as ethenyl, n-, i-propenyl, n-, sec-, i-, tert-butenyl.

$C_5$–$C_{12}$Cycloalkenyl is, for example, cyclopentenyl, cyclohexenyl, cycloheptenyl, cyclooctenyl, cyclononenyl, cyclodecenyl, cycloundecenyl, cyclododecenyl, preferably $C_5$–$C_8$cycloalkenyl such as cyclopentenyl, cyclohexenyl, cycloheptenyl, cyclooctenyl.

$C_2$–$C_{20}$Alkynyl is, for example, ethynyl, n-, i-propynyl, n-, sec-, i-, tert-butynyl, n-, neopentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, preferably $C_2$–$C_6$alkynyl such as ethynyl, n-, i-propynyl, n-, sec-, i-, tert-butynyl, n-, neo-pentynyl, n-hexynyl, particularly preferably $C_2$–$C_4$alkynyl such as ethynyl, n-, i-propynyl, n-, sec-, i-, tert-butynyl.

$C_6$–$C_{18}$Aryl is, for example, phenyl, 1-, 2-naphthyl, indenyl, azulenyl, acenaphthylenyl, fluorenyl, phenanthrenyl, anthracenyl, triphenylene, preferably phenyl.

$C_7$–$C_{18}$Aralkyl is, for example, benzyl, phenethyl, phenyl—(CH$_2$)$_{3-12}$—, preferably benzyl.

$C_1$–$C_{20}$Alkoxy is, for example, methoxy, ethoxy, n-, i-propoxy, n-, sec-, i-, tert-butoxy, n-, neopentoxy, hexoxy, heptoxy, octoxy, nonoxy, decoxy, undecoxy, dodecoxy, tridecoxy, tetradecoxy, pentadecoxy, hexadecoxy, heptadecoxy, octadecoxy, nonadecoxy, eicosoxy, preferably $C_1$–$C_6$alkoxy such as methoxy, ethoxy, n-, i-propoxy, n-, sec-, i-, tert-butoxy, n-, neopentoxy, n-hexoxy, 2,2-dimethylhexoxy, particularly preferably $C_1$–$C_4$alkoxy such as methoxy, ethoxy, n-, i-propoxy, n-, sec-, i-, tert-butoxy.

$C_1$–$C_{20}$Alkylamino is, for example, methylamino, ethylamino, n-, i-propylamino, n-, sec-, i-, tert-butylamino, n-, neopentylamino, hexylamino, heptylamino, octylamino, nonylamino, decylamino, undecylamino, dodecylamino, tridecylamino, tetradecylamino, pentadecylamino, hexadecylamino, heptadecylamino, octadecylamino, nonadecylamino, eicosylamino, preferably $C_1$–$C_6$alkylamino such as methylamino, ethylamino, n-, i-propylamino, n-, sec-, i-, tert-butylamino, n-, neopentylamino, n-hexylamino, particularly preferably $C_1$–$C_4$alkylamino such as methylamino, ethylamino, n-, i-propylamino, n-, sec-, i-, tert-butylamino.

$C_2$–$C_{20}$Dialkylamino is, for example, dimethylamino, diethylamino, n-, i-dipropylamino, n-, sec-, i-, tert-dibutylamino, n-, neodipentylamino, dihexylamino, diheptylamino, dioctylamino, dinonylamino, didecylamino, diundecylamino, didodecylamino, ditridecylamino, ditetradecylamino, dipentadecylamino, dihexadecylamino, diheptadecylamino, dioctadecylamino, dinonadecylamino, dieicosylamino, preferably $C_1$–$C_6$alkylamino such as dimethylamino, diethylamino, n-, i-dipropylamino, n-, sec-, i-, tert-dibutylamino, n-, neodipentylamino, n-dihexylamino, particularly preferably $C_1$–$C_4$alkylamino such as dimethylamino, diethylamino, n-, i-dipropylamino, n-, sec-, i-, tert-dibutylamino.

Phosphorus-containing $C_1$–$C_4$alkyl may preferably be diphenylphosphine radical-substituted methylene, ethylene, propylene or butylene such as —CH$_2$—Par$_2$ or —CH(Me)—Par$_2$, Ar being unsubstituted or substituted phenyl.

Diarylphosphine may be, for example, diphenylphosphine and substituted diphenylphosphines.

M$_2$ is, for example, a cation of a transition metal such as titanium, iron, ruthenium, osmium or nickel, preferably iron.

R$_3$ is particularly preferably one of the following radicals:

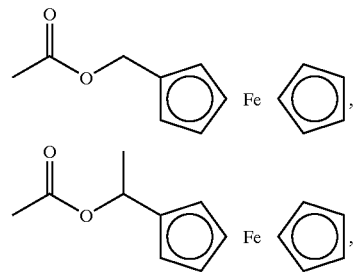

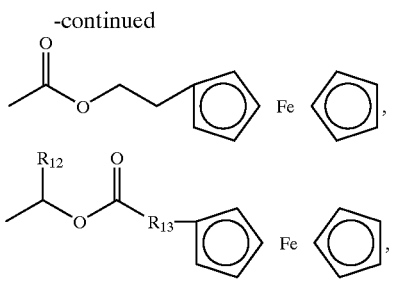

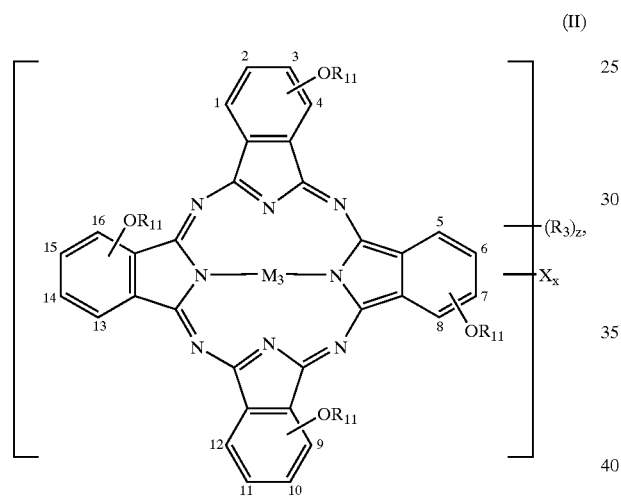

wherein $R_{12}$ may be hydrogen or methyl, and $R_{13}$ may be a single bond, —$CH_2$—, —$CH_2CH_2$—, —CH=CH—, —$CH_2$—C(=O)— or —$CH_2CH_2$—C(=O)—.

Very particularly preferred radicals $R_3$ are —C(=O)—O—$CH_2$—Cp—FeCp, —$CH_2$—O—C(=O)—$CH_2$—$CH_2$—C(=O)—Cp—FeCp, —$CH_2$O—C(=O)—Cp—FeCp or —$CH_2$—O—C(=O)—$CH_2$—Cp—FeCp.

Another preferred embodiment of this invention relates to metallocenyl-phthalocyanines of formula II wherein $R_{11}$ is $C_1$–$C_{12}$alkyl, particularly preferably branched $C_3$–$C_{12}$alkyl, more preferably 2,4-dimethyl-3-pentyl, and $M_3$ is palladium or copper, z is 1 or 2, and $R_3$ is the radicals mentioned above as being particularly or very particularly preferred.

The radicals —$OR_{11}$ may be in positions 1 to 16; the four radicals —$OR_{11}$ are preferably in each case in positions 1, 5, 9, 13 or 2, 6, 10, 14, the x halogen radicals, X and the z radicals $R_3$ being in the remaining free positions, preferably in para-position to the —$OR_{11}$ radicals. Particularly preferably, the four radicals —$OR_{11}$ are in positions (P1) 1, 5, 9, 13 ("$C_{4h}$"), and X, depending on x, is preferably in the positions selected from the group consisting of 4, 8, 12 and 16, and the z radicals $R_3$ are in para-position to one of the $OR_{11}$ radicals, i.e. for example in one of the free positions 4, 8, 12 or 16 not occupied by X. X may furthermore also be in positions 2, 3, 6, 7, 10, 11, 14 or 15.

This invention also embraces isomers and isomer mixtures. The —$OR_{11}$ radicals could, for example, also be in positions (P2) 1, 8, 9, 16 ("$D_{2h}$") or (P3) 1, 5, 12, 16 ("$C_{2v}$") or (P4) 1, 5, 9, 16 ("$C_s$"). Accordingly, a preferred embodiment of this invention also relates to isomer mixtures containing at least two, particularly preferably three, of the isomeric forms P1, P3 or P4.

The following compounds II serve as illustration:

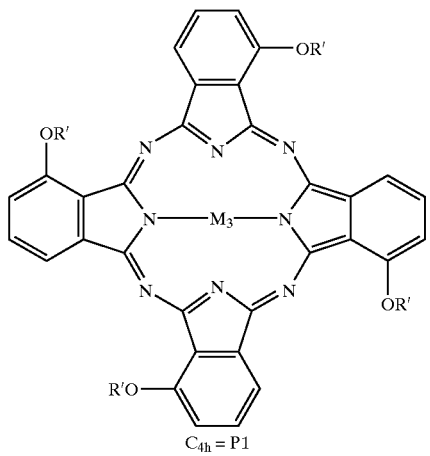

$C_{4h}$ = P1

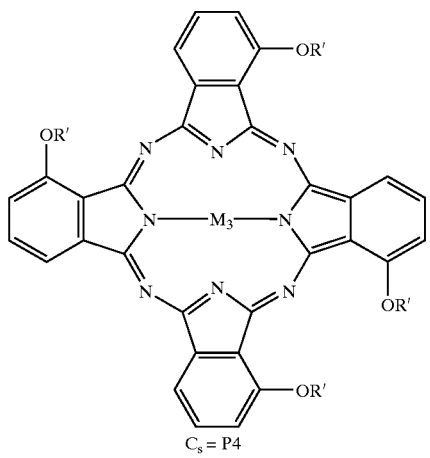

$C_s$ = P4

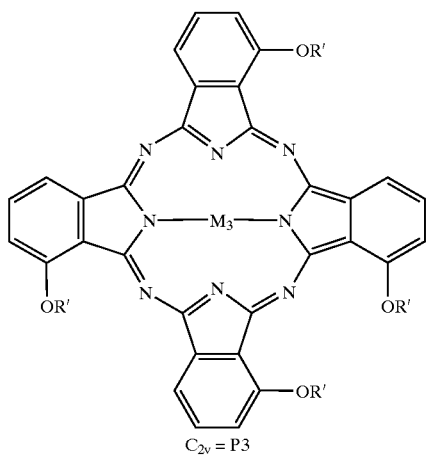

$C_{2v}$ = P3

-continued

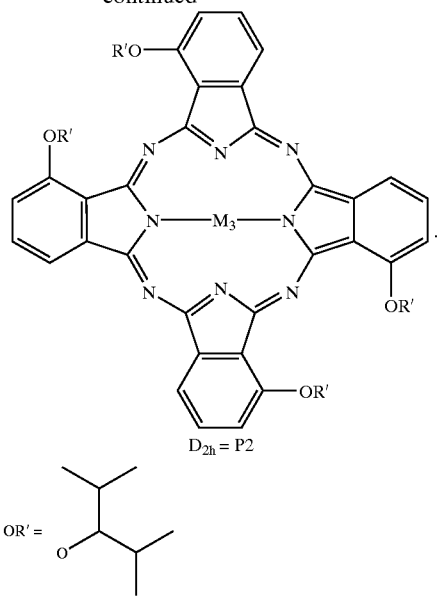

$D_{2h} = P2$ wherein: OR' = [isopropyl ether group structure]

Other isomers also result from $R_3$ (always under the condition that it is in para-position to the —$OR_{11}$ radical at the same benzene nucleus) facing an adjacent $OR_{11}$ radical (e.g. $R_3$ is in position 5, an —$OR_{11}$ radical is in position 4) or from $R_3$ not facing any adjacent —$OR_{11}$ radical (e.g. $R_3$ is in position 5 and there is no —$OR_{11}$ radical in position 4). Thus, in arrangement P1 ($C_{4h}$) there are only adjacent positions for $R_3$, whereas in arrangement P2 ($D_{2h}$) which, probably because of the steric hindrance of the —$OR_{11}$ radicals, is not found in practice, there are no adjacent positions to take. In arrangements P3 and P4 ($C_{2v}$ and $C_s$), however, there are two adjacent and two non-adjacent positions for $R_3$. It is self-evident that the arrangement of the halogen atoms X further increases the number of isomers.

A preferred embodiment of this invention relates to the compounds II, which contain one $R_3$ or two $R_3$, and to mixtures which contain one compound II containing one $R_3$ and one compound II containing two $R_3$. A preferred mixture is that which contains 1 to 25 mol %, particularly preferably 5 to 20 mol %, very particularly preferably 5 to 10 mol %, of a compound II containing two $R_3$, and 99 to 75 mol %, particularly preferably 95 to 80 mol %, very particularly preferably 95 to 90 mol %, of a compound II containing one $R_3$, the —$OR_{11}$, $R_3$, X and $M_3$ groups of the two compounds II being identical.

A very particularly preferred embodiment of this invention relates to metallocenyl-phthalocyanines of formula III

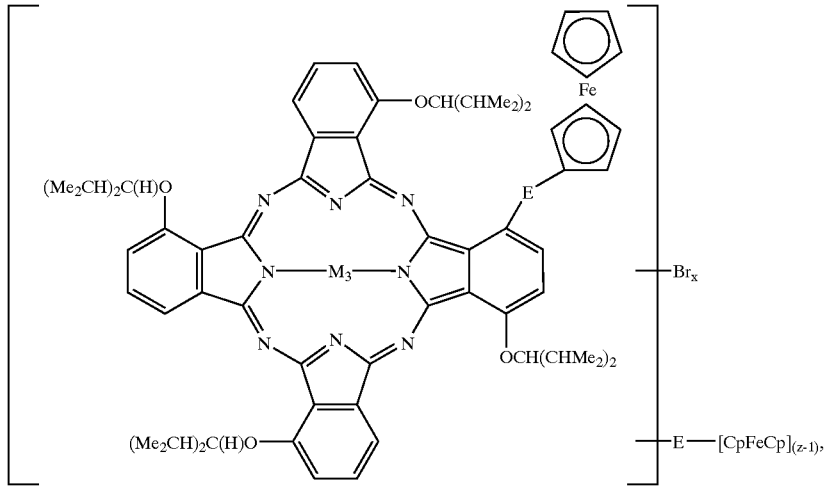

(III)

wherein E may be —$CH_2$—O—C(=O)— or —C(=O)—$OCH_2$—, the formula III presented here showing only one of the possible isomeric compounds (i.e. the arrangement P1 ($C_{4h}$) of the —$OR_{11}$ radicals, definition see above). This invention thus also embraces the isomeric compounds having the arrangements P3 or P4 ($C_{2v}$ or $C_s$), in particular a mixture containing three isomeric compounds having the P1, P3 and P4 arrangements of the —$OR_{11}$ radicals and compounds in which (z-1) is >0, for example 1, 2 or 3, preferably 1.

A very particularly preferred embodiment of this invention relates to

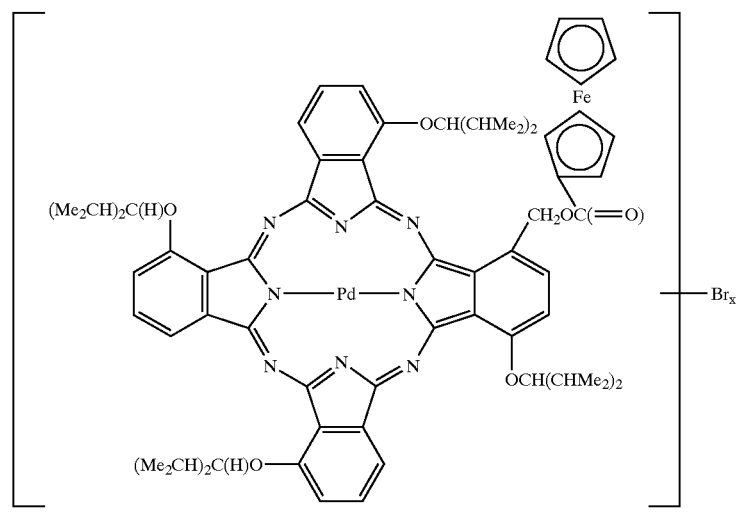

where X = 2.6 to 3.0, preferably 2.7 to 2.9, more preferably 2.8 and

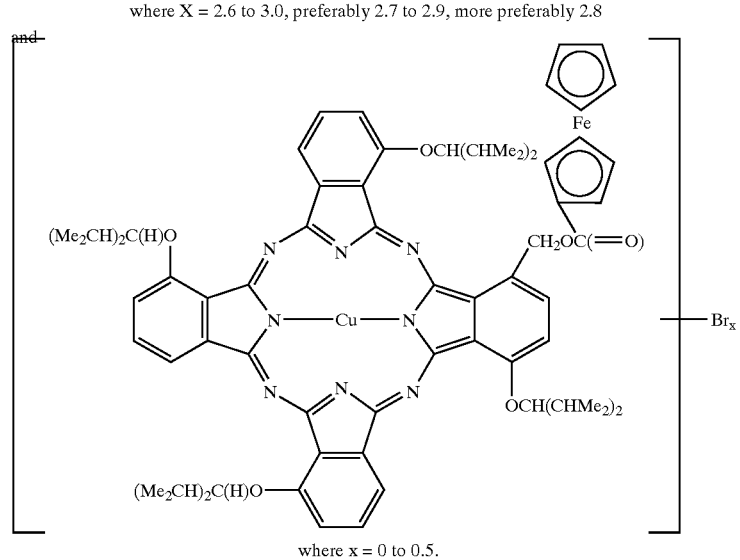

where x = 0 to 0.5.

Another preferred embodiment of this invention relates to mixtures containing at least one of the compounds II, preferably a mixture consisting of one compound II containing one $R_3$, one compound II containing two $R_3$ and one compound of formula IV

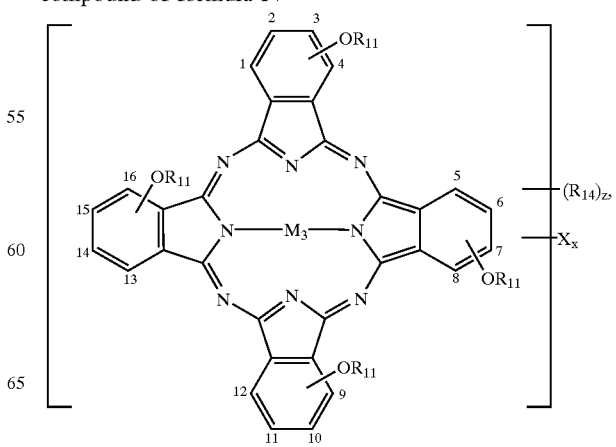

(IV)

wherein $R_{14}$ may be —CHO, —CH$_2$OH, —COOH, —CH$_2$OC(O)—C$_1$–C$_4$alkyl or an acetal such as —CH(O—C$_1$–C$_4$alkyl)$_2$, and z may be 1 or 2.

A particularly preferred embodiment of this invention relates to a mixture, which comprises (a) 60 to 95 mol %, preferably 80 to 95 mol %, of a compound II containing one $R_3$ (i.e. z=1), (b) 5 to 20 mol %, preferably 5 to 10 mol %, of a compound II containing two $R_3$ (i.e. z=2), and (c) 0 to 25 mol %, preferably 0 to 10 mol %, of a compound IV, wherein —OR$_{11}$, $R_3$=$R_{14}$, X and $M_3$ in formulae II and IV have the same meaning and the mol % amounts make up 100%.

Another preferred embodiment of this invention relates to mixtures, which comprise (a) 60 to 95 mol %, preferably 80 to 95 mol %, of a compound II, wherein $R_{11}$ is C$_1$–C$_{12}$alkyl and $M_3$ is palladium or copper, and z is 1, (b) 5 to 20 mol %, preferably 5 to 10 mol %, of a compound II containing two $R_3$ (z=2), and (c) 0 to 25 mol %, preferably 0 to 10 mol %, of a compound IV, wherein $R_{14}$ may be —CHO, —CH$_2$OH, —COOH, —CH$_2$OC(O)—C$_1$–C$_4$alkyl or an acetal, and z may be 1 or 2, wherein —OR$_{11}$, $R_3$=$R_{14}$, X and $M_3$ in formulae II and IV have the same meaning and the mol % amounts make up 100%.

Another preferred embodiment of this invention relates to mixtures which comprise at least one of the compounds III, preferably a mixture consisting of one compound III containing one radical —E—[CpFeCp] (i.e. z=1), one compound III containing two radicals —E—[CpFeCp] (i.e. z=2) and one compound of formula IV.

Accordingly, a particularly preferred embodiment of this invention also relates to a mixture, which comprises (a) 60 to 95 mol %, preferably 80 to 95 mol %, of a compound III containing a radical —E—[CpFeCp] (i.e. z=1)

(b) 5 to 20 mol %, preferably 5 to 10 mol %, of a compound III containing two radicals —E—[CpFeCp] (i.e. z=2) and (c) 1 to 25 mol %, preferably 1 to 10 mol %, of a compound IV, wherein —OR$_{11}$ in formula IV is —OCH(CHMe$_2$)$_2$, X is Br, and $M_3$ in formulae III and IV are identical and the mol % amounts make up 100%.

The compounds of this invention are usually obtained by esterifying a phthalocyanine with a metallocene derivative, for example in analogy to the method described in J.Chem.Soc., Chem.Commun. (1995)1715–1716, the phthalocyanine used being the phthalocyanine of formula V

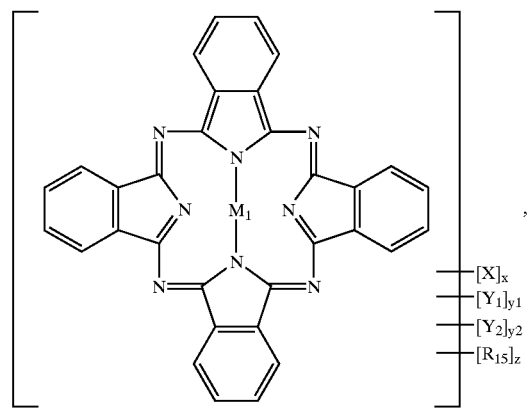

(V)

wherein $R_{15}$ may be a hydroxy-, carboxy- or acid chloride-containing radical, preferably —CH$_2$OH, —CH(Me)OH, —COOH, —COCl, and the metallocene derivative used being a compound selected from the group consisting of a hydroxy-, carboxy- and acid chloride-containing metallocene, preferably a metallocenecarbonyl chloride CpM$_2$Cp'—COCl, a metallocene-carboxylic acid CpM$_2$Cp'—COOH and a metallocene alcohol, the esterification usually being carried out in a manner known per se by reacting the phthalocyanine V (or the metallocene) containing a hydroxy-containing radical with the corresponding metallocene (or phthalocyanine) containing a carboxy- or acid chloride-containing radical, and wherein Cp is

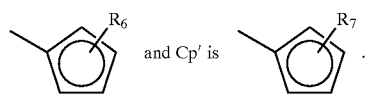

The other possible $R_3$ radicals which are indicated above are preferably accessible by analogous methods.

If the starting compounds V are —OH-carrying substituents, they are generally accessible by reduction from corresponding formyl compounds, preferably from the corresponding aldehyde, for example by the process described in WO 98/14520. The aldehyde reduction is preferably carried out using a complex metal hydride such as sodium borohydride. The reduction is particularly preferably carried out using a complex metal hydride based on an inert support material such as a zeolite, filter aids, silicates, aluminium oxides (alox), very particularly preferably using sodium borohydride on alox. The carboxyl group can be obtained by oxidation from the corresponding formyl compound in a manner known per se and from that, if desired, the corresponding acid chloride may be obtained.

The formyl compounds in turn are obtained, for example, also by process described in WO 98/14520 by reacting thephthalocyanines VI

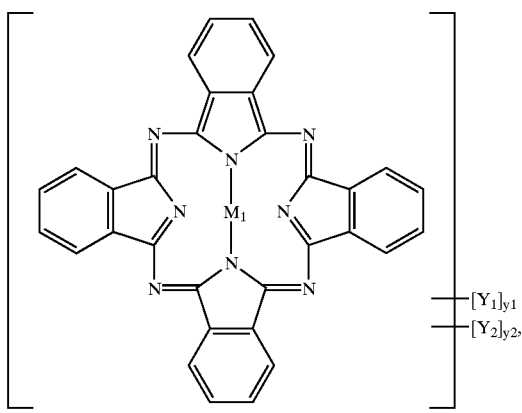

(VI)

which are known, inter alia, from EP-B 373 643, with phosphoroxy chloride/dimethylformamide or phosphoroxy chloride/N-methylformanilide.

The corresponding halogenated compounds I to V (x≠0) are obtained, for example, by halogenating the corresponding formyl compounds before reducing them to the corresponding alcohol compounds V.

The halogenation can be carried out by customary methods, such as those described in EP-A 513,370 or EP-A 519,419, for example by charging, if desired with heating, the correspondingly substituted phthalocyanines V or VI with bromine in an organic solvent such as saturated hydrocarbons, ethers or halogenated hydrocarbons or—as in the method described in EP-A 703,281—in a two-phase system consisting of water and a halogenated aromatic solvent which is essentially immiscible with water.

The metallocenecarbonyl compounds used may preferably be carbonyl chlorides such as ferrocenecarbonyl chloride and

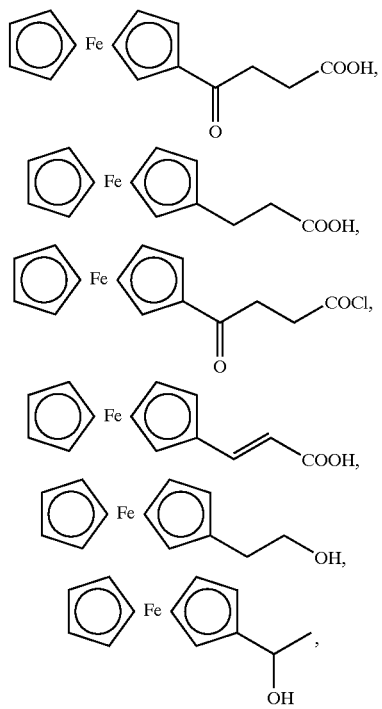

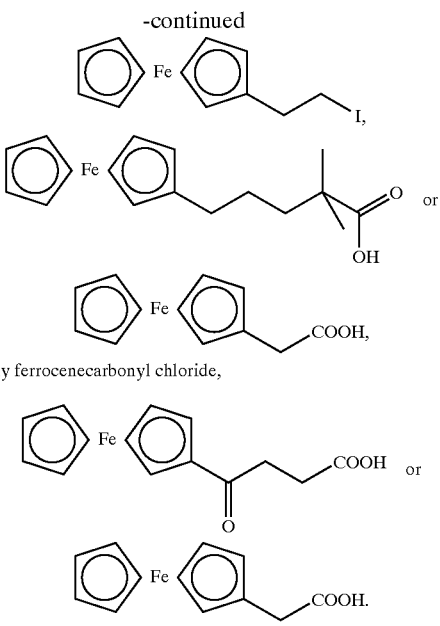

preferably ferrocenecarbonyl chloride,

Metallocenecarbonyl compounds are normally commercially available or are accessible in accordance with known instructions, such as those given in Org. Synthesis 56 (1977) 28–31.

The molar ratio of metallocenecarbonyl compound to compound V depends on the desired degree of esterification. It is preferred to choose a range from 5:1 to 0.5:1, particularly preferably from 2:1 to 1:1.

The reaction is usually carried out using a solvent. Solvents used are, for example, aprotic organic solvents such as pyridine, chlorobenzene, toluene, tetrahydrofuran, chloroform, methylene chloride or ethyl acetate, or mixtures thereof.

It is preferred to use basic solvents, especially if the esterification is carried out using acid chloride such as pyridine or tertiary amines, for example those which are cited in "Techniques of Chemistry", Vol. II, organic solvents, phys. properties and methods of purification, J. A. Riddick, W. B. Bunger, Th. K. Sakano, J. Wiley-Interscience Publication, 1986, in which case it is preferred to add a non-nucleophilic base, such as pyridine, or tertiary alkylamines, such as triethylamine. The ratio of base to acid chloride is usually chosen to be in the range from 1:1 to 10:1.

The ratio of solvent to compound V is usually chosen to be in the range from 2:1 to 30:1, preferably from 5:1 to 20:1.

The reaction temperature is usually chosen to be in the range from 0° C. to the reflux temperature under ambient pressure, preferably from room temperature to 100° C.

According to findings to date, the reaction pressure is not critical for the success of the invention. It is usefully chosen to be in the range from 70 kPa to 5 MPa, preferably from 90 to 120 kPa.

The reaction is preferably carried out under inert gas, such as nitrogen, or under a noble gas, such as neon or argon.

The compounds of this invention are also accessible by reducing the formyl compounds obtainable from the phthalocyanines VI by the method described in WO 98/14520 to the corresponding alcohol compounds, for example using sodium borohydride, and then esterifying them with a metallocenyl radical with subsequent halogenation.

It is also possible to first halogenise the formyl compounds, then to oxidise the formyl radicals to the carboxylic acid, subsequently to prepare the acid chloride therefrom and then to carry out esterification using a metallocenyl radical.

Finally, the formyl compounds can be oxidised to the corresponding carboxylic acid-containing phthalocyanines, the carboxylic acid unit can be reacted to the carboxylic acid chloride unit and can then be esterified with a metallocenyl radical and halogenised.

This invention also relates to an optical recording medium, which comprises a substrate, a recording layer, a reflecting or partly reflecting layer and, if desired, a protective layer, the recording layer containing a phthalocyanine of this invention.

If desired, the inventive optical recording medium can also contain more than one recording layer and/or more than one reflecting or partly reflecting (semitransparent) layer.

The substrate functioning as support for the layers applied to it is usually semitransparent (i.e. has a transparency T of at least 10%) or, preferably, transparent (T≧90%). The support may be 0.01 to 10 mm thick, preferably 0.1 to 5 mm thick.

The recording layer is preferably arranged between the transparent substrate and the reflecting layer. The recording layer is usually from 10 to 1000 nm thick, preferably from 50 to 500 nm thick, particularly preferably around 100 nm thick, for example from 80 to 150 nm thick. The absorption of the recording layer is usually from 0.1 to 2.0, preferably from 0.5 to 2.0, at the absorption maximum. With very particular preference, the layer thickness is chosen in a known manner, dependent on the respective refractive indices in the unwritten or written state at the readout wavelength, such that there is constructive interference in the unwritten state and destructive interference results in the written state, or vice versa.

The reflecting layer, which may usually be from 10 to 150 nm thick, preferably has high reflectivity (R≧70%) coupled with low transparency (T≦10%).

The layer which is topmost depending on the layer structure, for example the reflection layer or the recording layer, is preferably additionally provided with a protective layer, which usually can have a thickness in the range from 0.1 to 1000 $\mu$m, preferably from 0.1 to 50 $\mu$m and, particularly preferably, from 0.5 to 15 $\mu$m. This protective layer may, if desired, also serve as an adhesion promoter for a second substrate layer applied thereon, which is preferably from 0.1 to 5 mm thick and consists of the same material as the support substrate.

The reflectivity of the entire recording medium is preferably at least 60%, particularly preferably at least 65% at the writing wavelength of the laser used.

Examples of suitable substrates are glasses, minerals, ceramics and thermosets or thermoplastics. Preferred supports are glasses and homo- or copolymeric plastics. Examples of suitable plastics are thermoplastic polycarbonates, polyamides, polyesters, polyacrylates and polymethacrylates, polyurethanes, polyolefins, polyvinyl chloride, polyvinylidene fluoride, polyimides, duroplastic polyesters and epoxy resins. The substrate can be in pure form or can also contain customary additives, for example UV absorbers or dyes, as is proposed, inter alia, in JP 04/167 239, as light protection for the recording layer. In the latter case it may be convenient for the dye added to the support substrate to have an absorption maximum which is hypsochromically shifted by at least 10 nm, preferably by at least 20 nm, relative to the dye of the recording layer.

The substrate is preferably transparent in at least part of the range from 600 to 830 nm, so that it is permeable to at least 90% of the incident light of the writing or readout wavelength. On the side of the coating, the substrate preferably has a spiral guide groove with a groove depth from usually 50 to 500 nm, a groove width from usually 0.2 to 0.8 $\mu$m and a radial distance between 2 adjacent turns from usually 0.4 to 1.6 $\mu$m, particularly preferably having a groove depth from 100 to 300 nm and a groove width from 0.3 to 0.6 $\mu$m.

Instead of the substrate, the recording layer itself can have a guide groove, as is described, inter alia, in EP-A 392 531.

The recording layer preferably consists exclusively or essentially of one or more phthalocyanines of this invention. To increase the stability still further, however, it is also possible if desired to add known stabilisers in customary amounts, for example a nickel dithiolate described in JP 04/025 493 as light stabiliser. Additional dyes may optionally be added, although the amount of such dyes is conveniently not more than 50% by weight, preferably not more than 10% by weight, based on the recording layer. Since the advantages of the novel recording media are based on the novel phthalocyanines, it is useful for the optionally added dye to have a hypsochromically shifted absorption maximum relative to the novel phthalocyanine, and for the amount of the added dye to be kept so small that the proportion of the latter in the overall absorption of the recording layer in the region from 600 to 830 nm is not more than 20%, preferably not more than 10%. With particular preference, however, no additional dye is added.

A particularly suitable reflective material for the reflection layer comprises metals which are good reflectors of the laser radiation used for recording and reproduction, examples being the metals of the third, fourth and fifth main groups and subgroups of the Periodic Table of the chemical elements. Particularly suitable metals are Al, In, Sn, Pb, Sb, Bi, Cu, Ag, Au, Zn, Cd, Hg, Sc, Y, La, Ti, Zr, Hf, V, Nb, Ta, Cr, Mo, W, Fe, Co, Ni, Ru, Rh, Pd, Os, Ir, Pt and the lanthanide metals Ce, Pr, Nd, Pm, Sm, Eu, Gd, Tb, Dy, Ho, Er, Tm, Yb and Lu, and also their mixtures and alloys. For reasons of high reflectivity and ease of preparation, particular preference is given to a reflection layer of aluminium, silver, copper, gold or their alloys.

Suitable materials for the protective layer are predominantly plastics, which can be applied in a thin layer either directly or with the aid of adhesion layers to the support or the topmost layer. It is judicious to choose mechanically and thermally stable plastics having good surface properties, which can be additionally modified, for example written on. The plastics can either be thermosets or thermoplastics. Preference is given to radiation-cured (for example by means of UV radiation) protective layers, which are particularly easy and economic to prepare. Large numbers of radiation-curable materials are known. Examples of radiation-curable monomers and oligomers are acrylates and methacrylates of diols, triols and tetrols, polyimides of aromatic tetracarboxylic acids and aromatic diamines having $C_1$–$C_4$alkyl groups in at least two positions ortho to the amino groups, and oligomers containing dialkyl groups, for example dimethylmaleinimidyl groups.

The novel recording media can also feature additional layers, for example interference layers. It is also possible to construct recording media having a plurality of (for example two) recording layers. The construction and use of such materials are known to the skilled person. If such layers are present, preference is given to interference layers which are disposed between the recording layer and the reflecting layer and/or between the recording layer and the substrate and which consist of a dielectric material, for example as described in EP-A 353 393, consisting of $TiO_2$, $Si_3N_4$, ZnS or silicone resins.

The novel recording media can be prepared by processes known per se, it being possible to employ various coating methods depending on the materials used and on their functioning.

Examples of suitable coating methods are dipping, flow coating, spreading, knife coating and spin-coating, and also high-vacuum vapour deposition methods. When using flow coating methods, for example, solutions in organic solvents are generally used. When using solvents, care should be taken to ensure that the supports used are insensitive to these solvents. It is a particular advantage of the novel dyes that, even as pure compounds or as mixture of only few components, they are readily soluble in less polar solvents, making it possible to forego the use both of aggressive solvents such as acetone and of complicated isomeric mixtures. Suitable coating methods and solvents are described, inter alia, in EP-A 401 791.

The recording layer is preferably applied by spin-coating a dye solution, solvents that have been found appropriate being, in particular, alcohols such as 2-methoxyethanol, cyclopentanol, isopropanol, isobutanol, diacetone alcohol or n-butanol, preferably cyclopentanol, diacetone alcohol, or preferably, fluorinated alcohols such as 2,2,2-trifluorethanol or 2,2,3,3-tetrafluoro-1-propanol and also cyclohexane, methylcyclohexane and diisobutyl ketone, or mixtures thereof.

The metallic reflection layer is preferably applied by sputtering or vapour deposition under vacuum. The sputtering technique is particularly preferred on account of the high degree of adhesion to the support for the application of the metallic reflection layer. This technique is described in detail in textbooks (e.g. J. L. Vossen and W. Kern, "Thin Film Processes", Academic Press, 1978) as well as in the state of the art (e.g. EP-A 712 904), no further details thus needing to be provided here.

The structure of the novel recording medium depends principally on the readout methods; known functional principles are the measurement of the change in transmission or, preferably, in reflection.

If the recording material is constructed in accordance with the change in reflection, then the following structures are examples of those which can be employed: transparent support/recording layer (one or more layers)/reflection layer and, if useful, protective layer (not necessarily transparent), or support (not necessarily transparent)/reflection layer/recording layer and, if useful, transparent protective layer. In the former case the light is irradiated from the support side, while in the latter case the radiation is incident from the side of the recording layer or, if appropriate, from the side of the protective layer. In both cases the light detector is on the same side as the light source. The former construction of the recording material to be used in accordance with the invention is generally preferred.

If the recording material is constructed in accordance with the change in light transmission, the following alternative structure is a suitable example: transparent support/recording layer (one or more layers) and, if useful, transparent protective layer. The light for recording and for readout can be irradiated alternatively from the support side or from the side of the recording layer or, if appropriate, form the side of the protective layer, the light detector in this case always being on the opposite side.

Another embodiment of this invention therefore relates to an optical recording medium which comprises a novel metallocenyl-phthalocyanine or mixtures thereof or a metallocenyl-phthalocyanine prepared according to this invention.

A preferred embodiment of this invention relates to an optical recording medium, which consists of a transparent substrate, a recording layer on this substrate, a reflection layer on the recording layer and, if desired, a final protective layer, the recording layer comprising a metallocenyl-phthalocyanine, or mixtures thereof, which is novel or which is prepared according to this invention.

Recording (inscribing, writing) and reading out the information is preferably carried out using laser radiation.

Examples of suitable lasers are commercial available semiconductor diode lasers, typically GaAsAl, InGaAlP, GaAs or GaN laser diodes with a wavelength of 635, 650, 670, 680, 780 or 830 nm, or 390–430 nm, or gas/ion lasers, for example He/Ne, Kr, HeCd or Ar laser with a wavelength of 602, 612, 633, 647, or 442 and 457 nm.

Recording is preferably effected by inscribing pits of variable length using laser radiation which is pulse duration-modulated and focussed on the recording layer. The recording speed is chosen depending on the focus geometry and the laser performance and may be, for example, in the range from 0.01 to 100 m/s, preferably from 1–10 m/s.

The readout of the information is preferably carried out by spatially resolved measurement of the reflection or transmission using laser radiation of low capacity and a photodetector, it being particularly advantageous that laser radiation of the wavelength used for recording may be employed, so that no second laser apparatus need be used. Accordingly, in a preferred embodiment of the invention the information is recorded and read out at the same wavelength. During readout, the capacity of the laser is usually reduced over the laser radiation used for recording, e.g. from ten to fifty times. In the recording material used according to this invention, the information can be readout once or several times. Suitable photodetectors preferably include PIN and AV photodiodes as well as CCD (charge-coupled devices). The novel phthalocyanines make it possible to record information with a high degree of reliability and durability and these recordings are distinguished by having excellent mechanical and thermal stability, high stability to light and sharp edge zones of the optical pits. Particular advantages are the high signal/noise ratio as well as the high optical resolution which permits flawless recording and readout of the signals even at high speed ($\geq 4\times$) and at the same time with small jitter.

The novel medium is, in particular, an optical information medium of the WORM type. It can be used, for example, as a playable CD (compact disc), as recording material for computer and video appliances, as an identity and security card, or for the production of diffractive optical elements such as holograms.

This invention therefore also relates to the use of the novel recording medium for the optical recording, storage and reproduction of information, for the production of diffractive optical elements or for the recording of holograms. Recording and reproduction preferably take place in the wavelength range from 400 to 500 nm or, particularly preferably, from 600 to 830 nm.

Owing to the use of the novel dyes, the novel recording media have advantageously homogeneous, amorphous and low-scatter recording layers, the absorption edges of which are steep in the solid phase. Other advantages are the high light stability in daylight and under low laser radiation coupled with high sensitivity under high laser radiation, the uniform writing width, the good stability to heat and storage and, in particular, the high optical resolution and very small jitter.

EXAMPLES

Example 1

A 250 ml round-bottom three-necked flask, equipped with magnetic stirrer, thermometer, reflux condenser, nitrogen inlet and dropping funnel, is charged with 5 g (4.53 mmol) of monoformyltetra($\alpha$-2,4-dimethyl-3-pentyloxy) palladium-phthalocyanine (prepared according to Example A1 of WO-A 98/14520), 100 ml of chlorobenzene and 50 ml of water and this mixture is heated, with stirring, to 40° C. under an inert gas atmosphere. 2.17 g (13.59 mmol) of bromine are then added dropwise over 15 min and the reaction mixture is stirred for 1 hour at 60° C. The reaction mixture is then cooled to room temperature and diluted with 50 ml of methylene chloride. After separating the phases, the organic phase is washed once with 80 ml of water, once with 80 ml of 10% $NaHCO_3$ solution and once with 80 ml of 4% $NaHSO_3$ solution. The green solution obtained is charged with 50 g of silica gel and stirred for 15 min. After filtration, the filtrate is washed with toluene and concentrated by evaporation. The residue is dissolved in 25 ml of toluene and is added dropwise, with stirring, to 500 ml of methanol. The precipitate so obtained is collected by filtration, washed with 2×100 ml of methanol and dried overnight at 60° C./160 mbar, yielding 5.30 g (87.3% of theory) of brominated monoformyltetra(α-2,4-dimethyl-3-pentyloxy)palladium-phthalocyanine in the form of a green powder. Elemental analysis: 17.18% Br. UV (NMP): $\lambda_{max}$=718 nm, $\epsilon$=175670 l/mol·cm. IR: strong C=O bands at 1680 $cm^{-1}$.

Example 2

In a 500 ml round-bottom three-necked flask, equipped with magnetic stirrer, thermometer and nitrogen inlet, 5.30 g (3.95 mmol) of the brominated monoformyltetra(α-2,4-dimethyl-3-pentyloxy)palladium-phthalocyanine of Example 1 are dissolved in 250 ml of tetrahydrofuran/ethanol=1:1 and cooled, with stirring, to 5° C. under argon. 0.52 g (13.84 mmol) of sodium borohydride is then added and the reaction mixture is stirred for 2 hours at room temperature. The reaction mixture is then added dropwise, with stirring, to 750 ml of water and the precipitate obtained is collected by filtration, washed with 3×100 ml of water and dried overnight at 50° C./160 mbar, yielding 4.80 g (90.5% of theory) of brominated mono(hydroxymethyl)tetra(α-2,4-dimethyl-3-pentyloxy)palladium-phthalocyanine in the form of a green powder. Elemental analysis: 17.21% Br. UV (NMP): $\lambda_{max}$=722 nm, $\epsilon$=161320 l/mol·cm. IR: no signal of a C=O band. TGA: point of inflection of the decomposition curve: 320° C.

Example 3

A 50 ml round-bottom three-necked flask, equipped with magnetic stirrer, thermometer, reflux condenser, nitrogen inlet and dropping funnel, is charged with 1.5 g (1.41 mmol) of monoformyltetra(α-2,4-dimethyl-3-pentyloxy)copper-phthalocyanine (prepared according to Example A2 of WO-A 98/14520), 20 ml of chlorobenzene and 10 ml of water and this mixture is heated, with stirring, to 40° C. under argon. 0.225 g (1.41 mmol) of bromine is then added dropwise over 5 min and the reaction mixture is stirred for 1 hour at 60° C. The reaction mixture is then cooled to room temperature and diluted with 50 ml of toluene. After separating the phases, the organic phase is washed once with 20 ml of water, once with 20 ml of 10% $NaHCO_3$ solution, once with 20 ml of 4% $NaHSO_3$ solution and once with 20 ml of saturated NaCl solution. After drying over $MgSO_4$ and filtration, the filtrate is concentrated by evaporation. The residue is dissolved in 25 ml of toluene and added dropwise, with stirring, to 200 ml of methanol. The precipitate obtained is collected by filtration, washed twice with 50 ml of methanol and dried overnight at 60° C./160 mbar, yielding 1.12 g (69.7% of theory) of brominated monoformyltetra(α-2,4-dimethyl-3-pentyloxy)copper-phthalocyanine in the form of a green powder. Elemental analysis: 7.07% Br. UV (NMP): $\lambda_{max}$=715 nm, $\epsilon$=172900 l/mol·cm. IR: strong C=O bands at 1680 $cm^{-1}$.

Example 4

In a 100 ml round-bottom three-necked flask, equipped with magnetic stirrer, thermometer and nitrogen inlet, 1.07 g (0.95 mmol) of brominated monoformyltetra(α-2,4-dimethyl-3-pentyloxy)copper-phthalocyanine of Example 3 are dissolved in 50 ml of a mixture of tetrahydrofuran/ethanol=1:1 and cooled, with stirring, to 5° C. under argon. 0.126 g (3.33 mmol) of sodium borohydride is then added and the reaction mixture is stirred for 1.5 hours at room temperature. The reaction mixture is added dropwise, with stirring, to 200 ml of water and the precipitate obtained is collected by filtration and washed with 3×50 ml of water. The residue is dissolved in methylene chloride and then 10 g of silica gel are added and the solvent is removed by means of a rotary evaporator. The silica gel mixture is purified by chromatography (column diameter 3 cm, length 15 cm; hexane/ethyl acetate=9:1; flash chromatography), yielding 0.81 g (75.0% of theory) of brominated mono-(hydroxymethyl)tetra(α-2,4-dimethyl-3-pentyloxy)copper-phthalocyanine in the form of a green powder. Elemental analysis: 7.07% Br. UV (NMP): $\lambda_{max}$=717 nm, $\epsilon$=197390 l/mol·cm. IR: no signal of a C=O band. TGA: point of inflection of the decomposition curve: 330° C.

Example 5

A 25 ml round-bottom flask, equipped with magnetic stirrer and nitrogen inlet, is charged with 0.40 g (0.376 mmol) of mono(hydroxymethyl)tetra(α-2,4-dimethyl-3-pentyloxy)-copper-phthalocyanine (prepared according to Example A5 of WO-A 98/14520) in 10 ml of pyridine, and then 0.10 g (0.414 mmol) of ferrocenecarbonyl chloride (prepared according to Macromolecules 26 (1993) 1936–1940) is added and the green solution is stirred for 24 hours at room temperature under an inert gas atmosphere. Subsequently, the solvent is distilled off as an azeotrope using toluene. The crude product is purified via flash chromatography (column diameter=2 cm, hexane/ethyl acetate= 5:1), yielding a product mixture comprising (a) non-esterified, (b) a mono(hydroxymethyl)tetra(α-2,4-dimethyl-3-pentyloxy)copper-phthalocyanine (0.10 g (20.9% of theory), $R_f$=0.71), which is esterified with ferrocenecarboxylic acid (esterification amounts to 55% by weight, related to the product theoretically esterified to 100%), in the form of a green powder having the following physical properties: $\lambda_{max}$ (NMP)=716 nm, $\epsilon$=238590 l/mol·cm (extrapolated to the pure, 100% ester), elemental analysis: iron content= 2.42%, TGA: point of inflection of the decomposition curve=310° C., and (c) a mono(hydroxymethyl)tetra(α-2,4-dimethyl-3-pentyloxy)copper-phthalocyanine (0.30 g (62.6% of theory), $R_f$=0.28), which is esterified with ferrocenecarboxylic acid (esterification amounts to 26% by weight, related to the product theoretically esterified to 100%), in the form of a green powder having the following analytical values: $\lambda_{max}$ (NMP)=717 nm, $\epsilon$=234.060 l/mol·cm (extrapolated to the pure, 100% ester), elemental analysis: iron content=1.13%, TGA: point of inflection of the decomposition curve=320° C.

Example 6

A 25 ml round-bottom flask, equipped with magnetic stirrer and nitrogen inlet, is charged with 0.50 g (0.45 mmol) of mono(hydroxymethyl)tetra(α-2,4-dimethyl-3-pentyloxy)-palladium-phthalocyanine (prepared according to Example A4 of WO-A 98/14520) in 10 ml of pyridine, and then 0.123 g (0.49 mmol) of ferrocenecarbonyl chloride is added and the green solution is stirred for 14 hours at room temperature under an inert gas atmosphere and is then left to stand for three days at room temperature. Subsequently, the solvent is distilled off as an azeotrope using toluene. The residue is dissolved in 50 ml of toluene and is washed first with 20 ml of 1N HCl, then with 20 ml of a 10% NaHCO$_3$ solution, then with 20 ml of saturated NaCl solution and is finally dried over MgSO$_4$ and filtered. After concentrating the filtrate by evaporation, the crude product is purified via flash chromatography (column diameter=3 cm, hexane/ethyl acetate=9:1), yielding 0.269 g (45.0% of theory) of 44% by weight mono(hydroxymethyl)tetra(α-2,4-dimethyl-3-pentyloxy)palladium-phthalocyanine, which is esterified with ferrocenecarboxylic acid, in the form of a green powder having the following analytical values: $\lambda_{max}$ (NMP)=705 nm, $\epsilon$=241100 l/mol·cm (extrapolated to the pure, 100% ester). Elemental analysis: iron content=1.88%. TGA: point of inflection of the decomposition curve=330° C.

Example 7

A 25 ml round-bottom flask, equipped with magnetic stirrer and nitrogen inlet, is charged with 0.703 g (0.627 mmol) of brominated mono(hydroxymethyl)tetra(α-2,4-dimethyl-3-pentyloxy)copper-phthalocyanine having a bromine content of 7.07% (of Example 4) in 10 ml of pyridine, and then 0.174 g (0.70 mmol) of ferrocenecarbonyl chloride is added and the green solution is stirred for 24 hours at room temperature under an inert gas atmosphere. Subsequently, the solvent is distilled off as an azeotrope using toluene, and the residue is taken up in 50 ml of methylene chloride and is then washed in succession with 15 ml each of 1N HCl, 20 ml of saturated NaHCO$_3$ solution and with 2×20 ml of saturated NaCl solution, dried over MgSO$_4$ and filtered. After concentrating the filtrate by evaporation, the resulting crude product is purified via flash chromatography (column diameter=3 cm, hexane/ethyl acetate=9:1). The product is dissolved in 5 ml of toluene and is then dripped, with stirring, on 100 ml of methanol. The resulting precipitate is collected by filtration, washed twice with 20 ml of methanol and dried overnight at 60° C./160 mbar, yielding 0.467 g (56.9% of theory) of 81% by weight brominated mono (hydroxymethyl)tetra(α-2,4-dimethyl-3-pentyloxy)copper-phthalocyanine, which is esterified with ferrocenecarboxylic acid, in the form of a green powder having the following analytical values: $\lambda_{max}$ (NMP)=719 nm, $\epsilon$=190300 l/mol·cm (extrapolated to the pure, 100% ester). Elemental analysis: bromine content=6.74%, iron content=3.36%. IR: C=O bands at 1700 cm$^{-1}$.

TGA: point of inflection of the decomposition curve= 260° C.

Example 8

A 250 ml round-bottom flask, equipped with magnetic stirrer and nitrogen inlet, is charged with 4.68 g (3.49 mmol) of brominated mono(hydroxymethyl)tetra(α-2,4-dimethyl-3-pentyloxy)palladium-phthalocyanine having a bromine content of 17.21% (of Example 2) in 100 ml of pyridine, and then 1.30 g (5.23 mmol) of ferrocenecarbonyl chloride are added and the green solution is stirred for 24 hours at room temperature under an inert gas atmosphere. Subsequently, the solvent is distilled off as an azeotrope using toluene, and the residue is taken up in 250 ml of methylene chloride and washed in succession with 50 ml each of 1N HCl, 50 ml of a 10% NaHCO$_3$ solution and twice with 100 ml of water and is then dried over MgSO$_4$ and filtered. After concentrating the filtrate by evaporation, the crude product obtained is purified via flash chromatography (column diameter=4 cm, hexane/ethyl acetate=8:1). The purified product is dissolved in 20 ml of toluene and dripped, with stirring, on 300 ml of methanol. The resulting precipitate is collected by filtration and washed twice with 100 ml each of methanol and dried overnight at 60° C./160 mbar, yielding 4.31 g (79.4% of theory) of 77% by weight brominated mono (hydroxymethyl)tetra(α-2,4-dimethyl-3-pentyloxy) palladium-phthalocyanine, which is esterified with ferrocenecarboxylic acid, in the form of a green powder having the following analytical values: $\lambda_{max}$ (NMP)=722 nm, $\epsilon$=180 400 l/mol·cm (extrapolated to the pure, 100% ester). Elemental analysis: bromine content=15.25%, iron content= 2.78%. TGA: point of inflection of the decomposition curve=260° C.

Example 9

215.3 g (0.20 mol) of tetra(α-2,4-dimethyl-3-pentyloxy) palladium-phthalocyanine (prepared according to EP 703 280) are weighed into a 2.5 liter sulfonation flask, equipped with KPG stirrer, internal thermometer, reflux condenser, dropping funnel and nitrogen inlet, subsequently adding 320 ml of chlorobenzene and 162.2 g (1.20 mol) of N-methylformanilide under argon. To the green solution so obtained, 184.0 g (1.20 mol) of phosphoroxy chloride are added dropwise over 30 min at room temperature, the reaction solution being cooled by means of a water bath. This mixture is then stirred for 23 hours at room temperature. According to DC (hexane/ethyl acetate=4:1), only traces of the educt are present. 538 g (6.56 mol) of sodium acetate in 1.08 l of water are poured in very quickly, upon which the internal temperature rises to 73° C. The mixture is then stirred for 30 min. The two-phase mixture is transferred to a separating funnel and the reaction flask is washed with 300 ml of chlorobenzene. The colourless, aqueous lower phase is separated and the organic phase is charged with 200 g of silica gel and stirred for 30 min. After filtering through a filter aid, the filtrate is washed with 3×200 ml of chlorobenzene. The filtrate is concentrated by evaporation to 600 g of a solution and is poured, with stirring, on 4 l each of acetonitrile and stirred for 10 min. The precipitated product is subjected to filtration and the filter cake is washed with 3×400 ml of acetonitrile and is dried over the weekend at 60° C. and 125 torr, yielding 203.30 g (92.0% of theory) of green, powdery formylated tetra(α-2,4-dimethyl-3-pentyloxy)-palladium-phthalocyanine having the following analytical values: DC (silica gel 60, hexane/ethyl acetate= 4:1): R$_f$=0.69, 0.56 and 0.33; HPLC:<0.1% educt (percent per area), 93.4% monoaldehyde (percent per area), 6.6% dialdehyde (percent per area); UV/VIS (NMP): $\lambda_{max}$=702 nm, $\epsilon$=163606 l·mol$^{-1}$·cm$^{-1}$ Example 10

38.5 g (0.04 mol) of tetra(α-1,2-dimethylpropoxy) palladium-phthalocyanine (prepared according to EP 703 280) are weighed into a 350 ml sulfonation flask, equipped with KPG stirrer, internal thermometer, reflux condenser, dropping funnel and nitrogen inlet, subsequently adding 60 ml of chlorobenzene and 32.5 g (0.24 mol) of N-methylformanilide under argon. To the green solution so obtained, 36.8 g (0.24 mol) of phosphoroxy chloride are then added dropwise over 35 min at room temperature. The mixture is then stirred for 23 hours at room temperature and for 21 hours at 50° C. internal temperature. According to DC (hexane/ethyl acetate=4:1), only traces of the educt are present. The reaction mixture is poured, with stirring, to a solution of 96.3 g of sodium acetate in 190 ml of water, upon which the internal temperature rises to 65° C. The mixture is then stirred for 30 min. Subsequently, the two-phase mixture is transferred to a separating funnel and the reaction flask is washed with 100 ml of chlorobenzene. The colourless, aqueous lower phase is separated and the organic phase is charged with 50 g of silica gel and stirred for 30 min. After filtration, the filtrate is washed with 3×50 ml of chlorobenzene. Subsequently, the filtrate is concentrated by evaporation to 120 g of solution which is then poured, with stirring, on 1.2 l of acetonitrile and stirred for 10 min. The precipitated product is subjected to filtration and the filter cake is washed with 3×100 ml of acetonitrile and dried overnight at 60° C. and 125 torr, yielding 29.2 g (73.7% of theory) of a green, powdery formylated tetra(α-1,2-dimethylpropoxy)-palladium-phthalocyanine having the following analytical values: UV/VIS (NMP): $\lambda_{max}$=698 nm, $\epsilon$=168940 l·mol$^{-1}$·cm$^{-1}$ Elemental analysis: found: 5.68% H 63.76% C 11.34% N theor: 5.69% H 64.20% C 11.30% N IR: C=O bands at 1670 cm$^{-1}$ Example 11

A 5 l sulfonation flask, equipped with KPG stirrer, internal thermometer, dropping funnel, reflux condenser and nitrogen inlet, is charged under argon with 203.0 g (0.175 mol) of formylated tetra(α-2,4-dimethyl-3-pentyloxy)palladium-phthalocyanine in 2 l of chlorobenzene. 1 liter of water are then added and the two-phase solution is heated, with stirring, to 40° C. Subsequently, 79.69 g (0.50 mol) of bromine are added dropwise over 15 minutes. The reaction mixture is then heated to 60° C. and stirred for 60 min. After cooling the reaction mixture to room temperature, 1 liter of water is added and the stirrer is then turned off and the water phase is removed by suction filtration (pH=1). 1 liter of water is then added, stirred briefly and is again subjected to suction filtration. This is repeated twice. Prior to the last suction filtration, the two-phase system is transferred to a separating funnel and washed with a small amount of chlorobenzene. The phases are separated and 37 g of sodium bisulfite are added to the organic phase and stirred for 10 min. Subsequently, 200 g of silica gel are added and stirred for 15 min. The mixture is then filtered over a Büchner filter and washed with 3×200 ml of chlorobenzene. The filtrate is concentrated by evaporation to 600 g of solution and is dripped, with stirring, on 4 l of acetonitrile. The precipitated product is subjected to filtration and the filter cake is washed with 3×400 ml of acetonitrile and dried overnight at 60° C. and 125 torr, yielding 209.5 g (89.3% of theory) of green, powdery, brominated and formylated tetra(α-2,4-dimethyl-3-pentyloxy)palladium-phthalocyanine having the following analytical values: DC (silica gel 60, hexane/ethyl acetate=4:1): $R_f$=0.64, 0.54, 0.48, 0.34 Elemental analysis: 16.29% Br UV/VIS (NMP): $\lambda_{max}$=718 nm, $\epsilon$=174170 l·mol$^{-1}$·cm$^{-1}$ Example 12

A 750 ml sulfonation flask, equipped with KPG stirrer, internal thermometer, dropping funnel, reflux condenser and nitrogen inlet, is charged under argon with 29.0 g (29.2 mmol) of formylated tetra(α-1,2-dimethylpropoxy) palladium-phthalocyanine in 350 ml of chlorobenzene, and then 175 ml of water are added and the two-phase solution is heated, with stirring, to 40° C. 13.05 g (81.66 mmol) of bromine are then added dropwise over 15 min. The reaction mixture is then heated to 60° C. and stirred for 60 min. After cooling the reaction mixture to room temperature, the stirrer is turned off and the water phase (pH=1) is removed by suction filtration. Subsequently, 250 ml of water are added and the mixture is stirred briefly and again subjected to suction filtration, which procedure is repeated twice. Prior to the final suction filtration, the two-phase system is transferred to a separating funnel and washed with a small amount of chlorobenzene. The phases are separated and 3 g of sodium bisulfite are added to the organic phase and this mixture is stirred for 10 min. Subsequently, 30 g of silica gel are added and stirred for 15 min. The mixture is then filtered over a Büchner filter and washed with 3×50 ml of chlorobenzene. The filtrate is concentrated by evaporation to 60 g of solution and is then dripped, with stirring, on 1 liter of acetonitrile. The precipitated product is collected by filtration and the filter cake is washed with 3×100 ml of acetonitrile and dried overnight at 60° C. and 125 torr, yielding 24.23 g (67.6% of theory) of green, powdery, brominated and formylated tetra(α-1,2-dimethylpropoxy)palladium-phthalocyanine having the following analytical values: Elemental analysis: 18.93% Br UV/VIS (NMP): $\lambda_{max}$=708 nm, $\epsilon$=174560 l·mol$^{-1}$·cm$^{-1}$ IR: C=O bands at 1670 cm$^{-1}$ Example 13

A 2.5 l sulfonation flask, equipped with anchor stirrer, internal thermometer and nitrogen inlet, is charged under argon with 3.69 g (97.6 mmol) of sodium borohydride in 22 ml of diethylene glycol dimethyl ether (puriss, absolute) and the mixture is stirred. Most of the reagent dissolves and a gel-like mixture forms. 36.9 g of alox (neutral, activity 1) are then added, upon which a solid forms immediately which is briefly mixed with a spatula. Subsequently, 1.1 liter of tetrahydrofuran and 109.0 g (81.3 mmol) of brominated and formylated tetra(α-2,4-dimethyl-3-pentyloxy)palladium-phthalocyanine are added. The suspension is then vigorously stirred at room temperature. The reaction is followed by means of DC (hexane/ethyl acetate=4:1) until only traces of the educt are visible. After a reaction time of 22 hours, the reaction mixture is filtered through a filter aid and the residue is washed with 3×100 ml THF. The filtrate is transferred to a 2.5 l sulfonation flask, equipped with anchor stirrer, internal thermometer, dropping funnel and distillation head, and is charged dropwise with 25 g of acetic acid, slight evolution of gas being observed. After that, the pH is about 5. 700 ml of toluene are then added and the THF is removed by distillation in an oil bath of 130° C. until the overhead temperature is 90° C. After cooling the mixture to 60° C., 250 ml of saturated NaCl solution are poured in and the mixture is stirred for 10 min. The warm mixture is then transferred to a separating funnel and the phases are separated. The organic phase is charged with 109 g of silica gel and stirred for 15 min. This mixture is then filtered and the filter product is washed with 3×100 ml of toluene. Using a rotary evaporator, the filtrate is concentrated by evaporation to 300 g of solution and is then poured, with stirring, on 3.0 l of acetonitrile. After stirring for 10 min, the precipitated product is collected by filtration and washed with 3×200 ml of acetonitrile. The product is dried overnight at 60° C. and 125 torr, yielding 99.5 g (91.2% of theory) of green, powdery, brominated and hydroxy-methylated tetra(α-2,4-dimethyl-3-pentyloxy)palladium-phthalocyanine having the following analytical values: Elemental analysis: 15.90% Br UV/VIS (NMP): $\lambda_{max}$=723 nm, $\epsilon$=163590 l·mol$^{-1}$·cm$^{-1}$ IR: no C=O bands of the aldehyde (1680 cm$^{-1}$) visible Example 14

A 750 ml sulfonation flask, equipped with anchor stirrer, internal thermometer, reflux condenser and nitrogen inlet, is charged under argon with 0.95 g (25.17 mmol) of sodium borohydride in 5.6 ml of diethylene glycol dimethyl ether (puriss, absolute) and stirred. Most of the reagent dissolves and a gel-like mixture forms. 9.5 g of alox (neutral, activity 1) are then added, upon which a solid forms immediately which is briefly mixed using a spatula. Subsequently, 280 ml of tetrahydrofuran and 24.1 g (19.62 mmol) of brominated and formylated tetra(α-1,2-dimethylpropoxy)palladium-phthalocyanine are added. The suspension is then vigorously stirred at room temperature. The reaction is followed via thin-layer chromatography (hexane/ethyl acetate=4:1) until only traces of the educt are visible. After a reaction time of 1.5 hours, the reaction mixture is filtered through a filter aid and the residue is washed with 3×50 ml of THF. The filtrate is transferred to a 1.5 l sulfonation flask, equipped with anchor stirrer, internal thermometer, dropping funnel and distillation head, and is charged dropwise with 10 ml of acetic acid, a slight evolution of gas being observed. After that, the pH is about 5. 500 ml of toluene are added and the THF is removed by distillation in an oil bath of 150° C. until the overhead temperature is 95° C. After cooling to 60° C., 250 ml of saturated NaCl solution are poured in and the mixture is stirred for 10 min. The warm mixture is transferred to a separating funnel and the phases are separated. The organic phase is charged with 30 g of silica gel and stirred for 15 min. After filtration, the filter product is washed with 3×50 ml of toluene. Using a rotary evaporator, the filtrate is concentrated by evaporation to 75 g of a solution which is then poured, with stirring, on 1.0 l of acetonitrile. After stirring for 10 min, the precipitated product is collected by filtration and washed with 3×50 ml of acetonitrile. The product is dried overnight at 60° C. and 125 torr, yielding 21.5 g (89.0% of theory) of green, powdery, brominated and hydroxy-methylated tetra($\alpha$-1,2-dimethylpropoxy)palladium-phthalocyanine having the following analytical values: Elemental analysis: 18.48% Br UV/VIS (NMP): $\lambda_{max}$=713 nm, $\epsilon$=165490 l·mol$^{-1}$·cm$^{-1}$ IR: no C=O bands of the aldehyde (1680 cm$^{-1}$) visible

Example 15

A 2 l round-bottom flask, equipped with magnetic stirrer and nitrogen inlet, is charged with 38.0 g (0.152 mol) of ferrocenecarboxylic acid chloride (prepared by a process slightly modified from Macromolecules 26 (1993) 1936–1940), 780 ml of pyridine, 97.3 g (72.48 mmol) of brominated and hydroxymethylated tetra($\alpha$-2,4-dimethyl-3-pentyloxy)palladium-phthalocyanine and 0.885 g (7.25 mmol) of 4-dimethylaminopyridine under argon, and the dark green solution is stirred for 20 hours at room temperature. The reaction mixture is then poured, with vigorous stirring, on 8 l of water and the precipitate is collected by filtration and washed with 3×200 ml of water. After drying the residue overnight at 60° C. and 125 torr, it is dissolved in 600 ml of toluene and then 100 g of silica gel are added and the mixture is stirred for 15 minutes. The suspension is filtered and the residue is washed with 3×100 ml of toluene. Using a rotary evaporator, the filtrate is concentrated by evaporation to 370 g of a solution which is then poured, with stirring, on 3.7 l of acetonitrile and stirred for 10 minutes. The precipitate is collected by filtration, washed with 3×200 ml of acetonitrile and dried overnight at 60° C./125 T, yielding 109.8 g (97.5% of theory) of a green, powdery, brominated and hydroxymethylated tetra($\alpha$-2,4-dimethyl-3-pentyloxy)palladium-phthalocyanine, which is esterified with ferrocenecarboxylic acid, having the following analytical values: Elemental analysis: 13.33% Br, 4.40% Fe UV/VIS (NMP): $\lambda_{max}$=722 nm, $\epsilon$=170120 l·mol$^{-1}$·cm$^{-1}$ IR: C=O bands for ester present TGA: point of inflection of the decomposition curve=257° C.

Example 16

A 500 ml round-bottom flask, equipped with magnetic stirrer and nitrogen inlet, is charged with 7.0 g (28.17 mmol) of ferrocenecarboxylic acid chloride (prepared by a process slightly modified from Macromolecules 26 (1993) 1936–1940), 190 ml of pyridine, 16.23 g (13.19 mmol) of brominated and hydroxymethylated tetra($\alpha$-1,2-dimethylpropoxy)-palladium-phthalocyanine and 0.172 g (1.41 mmol) of 4-dimethylaminopyridine under argon, and the dark green solution is stirred for 20 hours at room temperature. The reaction mixture is then poured, with thorough stirring, on 1.8 l of water and the precipitate is collected by filtration and washed with 3×200 ml of water. After drying the residue overnight at 60° C. and 125 torr, it is dissolved in 200 ml of toluene and then 32 g of silica gel are added and the mixture is stirred for 15 minutes. The suspension is filtered and the residue is washed with 3×50 ml of toluene. Using a rotary evaporator, the filtrate is concentrated by evaporation to 60 g of a solution which is then poured, with stirring, on 800 ml of acetonitrile and stirred for 10 minutes. The precipitate is collected by filtration, washed with 3×50 ml of acetonitrile and dried overnight at 60° C. and 125 torr, yielding 17.66 g (92.8% of theory) of a green, powdery, brominated and hydroxymethylated tetra($\alpha$-1,2-dimethylpropoxy)palladium-phthalocyanine, which is esterified with ferrocenecarboxylic acid, having the following analytical values: Elemental analysis: 15.52% Br, 4.23% Fe UV/VIS (NMP): $\lambda_{max}$=711 nm, $\epsilon$=163400 l·mol$^{-1}$·cm$^{-1}$ IR: C=O bands for ester (1720 cm$^{-1}$) present TGA: point of inflection of the decomposition curve=262° C.

Example 17

A 50 ml round-bottom flask, equipped with magnetic stirrer and nitrogen inlet, is charged with 0.50 g (0.19 mmol) of ferrocene acetic acid chloride (prepared in analogy to a process slightly modified from Macromolecules 26 (1993) 1936–1940), 10 ml of pyridine, 1.28 g (0.95 mmol) of brominated and, hydroxymethylated tetra($\alpha$-2,4-dimethyl-3-pentyloxy)-palladium-phthalocyanine and 12 mg (0.1 mmol) of 4-dimethylaminopyridine under argon, and the dark green solution is stirred for 20 hours at room temperature. The reaction mixture is then poured, with thorough stirring, on 100 ml of water and the precipitate is collected by filtration and washed with 4×50 ml of water. After drying the residue for 4 hours at 60° C. and 125 torr, it is dissolved in 15 ml of toluene and then 1.3 g of silica gel are added and the mixture is stirred for 10 minutes. The suspension is filtered and the residue is washed with 3×10 ml of toluene. Using a rotary evaporator, the filtrate is concentrated by evaporation to 4.8 g of a solution which is then poured, with stirring, on 49 ml of acetonitrile and stirred for 10 minutes. The precipitate is collected by filtration, washed with 3×50 ml of acetonitrile and dried overnight at 60° C. and 125 torr, yielding 1.2 g (80.5% of theory) of a green powder (brominated and hydroxymethylated tetra($\alpha$-2,4-dimethyl-3-pentyloxy)palladium-phthalocyanine which is esterified with ferrocene acetic acid) having the following analytical values: Elemental analysis: 12.71% Br, 4.49% Fe UV/VIS (NMP): $\lambda_{max}$=723 nm, $\epsilon$=148170 l·mol$^{-1}$·cm$^{-1}$ IR: C=O band for ester (cm$^{-1}$) present TGA: point of inflection of the decomposition curve=278° C.

Example 18

A 2% by weight solution of the compound of Example 8 in a mixture consisting of methylcyclohexanone and 2,6-dimethyl-4-heptanone (98:2) is filtered through a Teflon filter having a pore width of 0.2 $\mu$m and is applied to the surface of a 1.2 mm thick, grooved disc (groove depth 195 nm, groove width 500 nm, track distance 1.6 $\mu$m) by the spin-coating process at a rotational speed of 400 rpm. The excess of the solution is centrifuged off by increasing the rotational speed. The evenly applied layer is then dried in a circulating air oven at 70° C. for 20 min. In a vacuum coating apparatus (Twister, Balzers), a 60 nm thick gold layer is then sprayed onto the recording layer so obtained. Onto this layer is then coated a 5 $\mu$m thick protective layer consisting of a UV-curable photopolymer (SD-220, of Dainippon Ink) via spin-coating. Different video sequences are written onto the disc produced in this manner at a writing speed of 1x using a commercially available HP CD-Writer 6020. The dynamic signal parameters are determined by means of a fully automatic CD test system (CD-Cats, Audio Development) and are compiled in the following Table A for the different speeds.

Example 19

Example 18 is repeated, but at a writing speed of 2×. The measurement results are given in the following Table A.

Example 20

Example 18 is repeated, but the data are inscribed at a writing speed of 4× on a commercially available recorder (Yamaha $CDR_{100}$). The measurement results are given in the following Table A.

Example 21

Example 18 is repeated, but the data are inscribed at a speed of 6× on a commercially available recorder (Kodak PCD Writer 600). The measurement results are given in the following Table A.

TABLE A

| recording speed | 1× | | 2× | | 4× | | 6× | |
|---|---|---|---|---|---|---|---|---|
| pit length | 3T | 11T | 3T | 11T | 3T | 11T | 3T | 11T |
| land jitter [ns] | 29 | 27 | 28 | 22 | 35 | 28 | 35 | 31 |
| BLER | | 6 | | 3 | | 4 | | 7 |

Example 22

A 2.5% by weight solution of the compound of Example 8 in a mixture consisting of di-n-butyl ether and 2,6-dimethyl-4-heptanone (at a volume ratio of 98:2) is filtered through a Teflon filter having a pore width of 0.2 mm and is applied to the surface of a 1.2 mm thick, grooved disc (groove depth 200 nm, groove width 560 nm, track distance 1.6 mm) by the spin-coating process at a rotational speed of 525 rpm. The excess of the solution is removed by raising the rotational speed. The evenly applied layer is then dried in a circulating air oven at 70° C. for 20 min. In a vacuum coating apparatus (Swivel, Balzers), a 60 nm thick silver layer is then applied by spraying onto the recording layer so obtained. An 8 mm thick protective layer consisting of a UV-curable photopolymer is then spin-coated on this layer. Different data are inscribed on the disc produced in this manner at a writing speed of 1× on a commercially available recorder (Philips CDD3610). The dynamic signal parameters are determined via a fully automatic CD test system (CD-Cats SA3, Audio Development) and are listed in the following Table B for the different speeds.

Example 23

Example 22 is repeated, but the data are inscribed at a writing speed of 4× on a commercially available recorder (Yamaha $CDR_{400}$). The measurement results are given in the following Table B.

Example 24

Example 22 is repeated, but the data are inscribed at a writing speed of 6× on a commercially available recorder (Kodak PCD 600). The measurement results are given in the following Table B.

Example 25

Example 22 is repeated, but the data are inscribed at a writing speed of 8× on a commercially available recorder (Sanyo CRD-R 820). The measurement results are given in the following Table B.

TABLE B

| recording speed | 1× | | 4× | | 6× | | 8× | |
|---|---|---|---|---|---|---|---|---|
| pit length | 3T | 11T | 3T | 11T | 3T | 11T | 3T | 11T |
| land jitter [ns] | 28 | 30 | 24 | 21 | 33 | 29 | 29 | 25 |
| pit jitter [ns] | 23 | 23 | 28 | 26 | 28 | 22 | 25 | 23 |
| BLER | | 1 | | 0 | | 3 | | 2 |

What is claimed is:

1. A process for the manufacture of an optical recording medium having at least one recording layer, comprising the steps of a) incorporating a metallocenyl-phthalocyanine represented by formula I

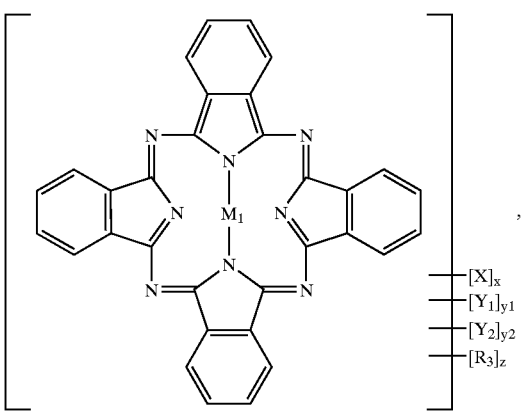

(I)

wherein $M_1$ is a divalent metal, an oxometal group, halogenometal group or hydroxymetal group, or two hydrogen atoms, X is halogen $Y_1$ is —$OR_1$, —OOC—$R_2$, —$NHR_1$, —$N(R_1)R_2$, $Y_2$ is —$SR_1$, $R_3$ is

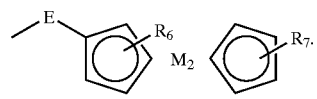

$R_6$ and $R_7$ are each independently of the other hydrogen, halogen, $C_1$–$C_4$alkyl, $C_1$–$C_4$alkoxy, amino-$C_1$–$C_4$alkyl, diarylphosphine, or phosphorus-containing $C_1$–$C_4$alkyl, $M_2$ is a transition metal cation, x may be a rational number from 0 to 8

$y_1$ and $y_2$ may be each independently of the other a rational number from 0 to 6 z may be a number from 1 to 4, wherein $(x+y_1+y_2+z)$ is $\leq 16$, and wherein $R_1$ and $R_2$ may be each independently of the other $C_1$–$C_{20}$alkyl which is unsubstituted or substituted by halogen, hydroxy, $C_1$–$C_{20}$alkoxy, $C_1$–$C_{20}$alkylamino or $C_2$–$C_{20}$dialkylamino and which may be interrupted by —O—, —S—, —NH— or —$NR_{10}$—, wherein $R_{10}$ may be $C_1$–$C_6$alkyl, $C_5$–$C_{20}$cycloalkyl, $C_2$–$C_{20}$alkenyl, $C_5$–$C_{12}$cycloalkenyl, $C_2$–$C_{20}$alkynyl, $C_6$–$C_{18}$aryl or $C_7$–$C_{18}$aralkyl, and wherein one or two ligands may optionally be bound to the divalent metal atom, the oxometal group, halogenometal group or hydroxymetal group, and E is composed of a chain of at least two members selected from the group consisting of —$CH_2$—, —C(=O)—, —CH($C_1$–$C_4$alkyl)—, —C($C_1$–$C_4$alkyl)$_2$—, —NH—, —S—, —O— and —CH=CH— into said record layer, wherein the substrate is a homo- or copolymeric plastic.

2. A process according to claim 1 wherein the metallocenyl-phthalocyanine compound is represented by formula

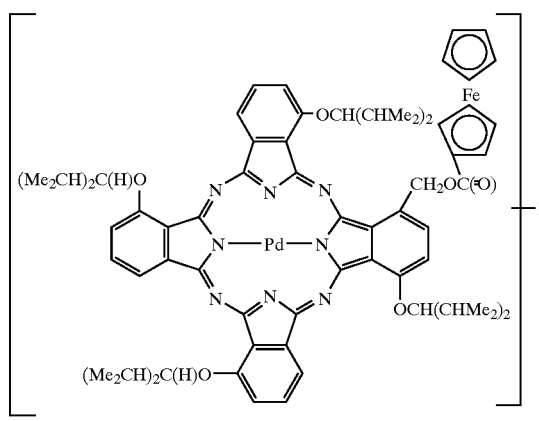

where x = 2.6 to 3.0.

3. A process according to claim 1 wherein the metallocenyl-phthalocyanine compound is represented by formula

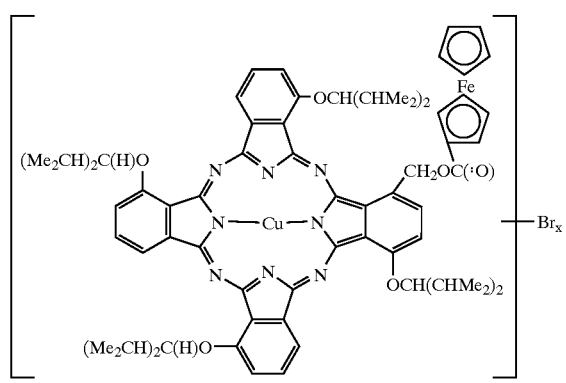

where x = 0 to 0.5.

4. A process according to claim 1 wherein the optical recording medium is a DVD, a diffractive-optical element or medium for recording a hologram.

5. A process for the manufacture of an optical recording medium according to claim 1 having at least one recording layer, comprising the steps of a) incorporating a mixture, which comprises (a) 60 to 95 mol % of a compound II

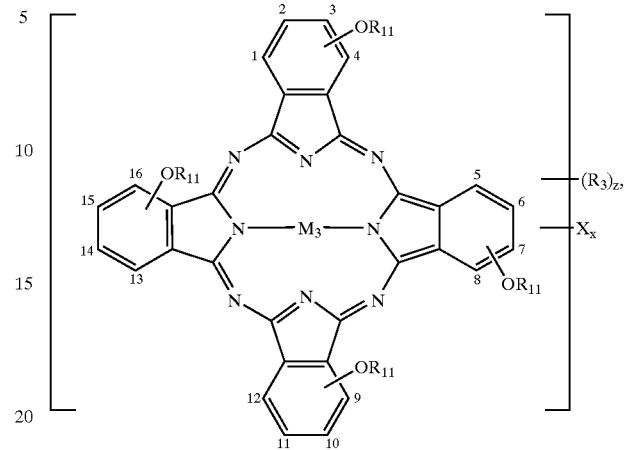

containing one radical $R_3$ (z=1), $R_{11}$ is $C_1$–$C_{12}$ alkyl and $M_3$ has the same meaning as $M_1$, (b) 5 to 20 mol % of a compound II containing two radicals $R_3$ (z=2), and (c) 0 to 25 mol % of a compound IV

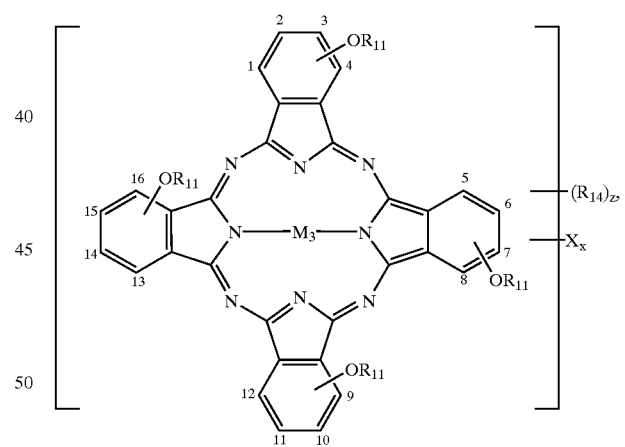

Wherein $R_{14}$ may be —CHO, —$CH_2$OH, —COOH, —$CH_2$OC(O)—$C_1$–$C_{12}$ alkyl or an acetal, an z may be 1 or 2, wherein —$OR_{11}$, X and $M_3$ each have the same meaning in formulae II and IV and are as defined in claim 8, the mol-% amounts making up 100%, into said recording layer.

6. A process according to claim 5 wherein the optical recording medium is a DVD, a diffractive-optical element or medium for recording a hologram.

7. A process for the manufacture of optical recording medium according to claim 1 having at least one recording layer, comprising the steps of a) incorporating a mixture, which comprises
(a) 60 to 95 mol % of a compound II

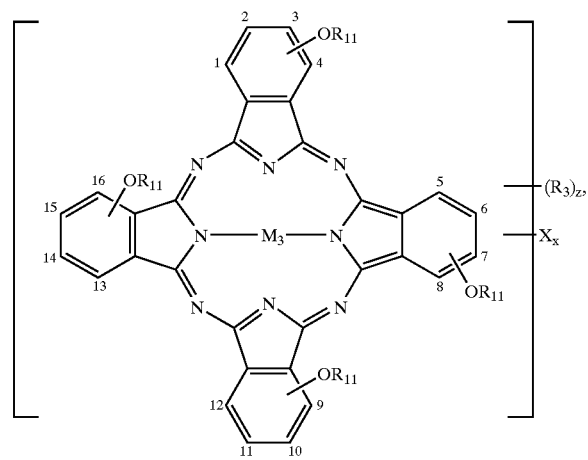

containing one radical $R_3$ (z=1),
wherein $R_{11}$ is $C_1-C_{12}$alkyl and $M_3$ is palladium or copper, and z is 1, (b) 5 to 20 mol % of a compound II containing two $R_3$ (z=2), and
(c) 0 to 25 mol % of a compound IV

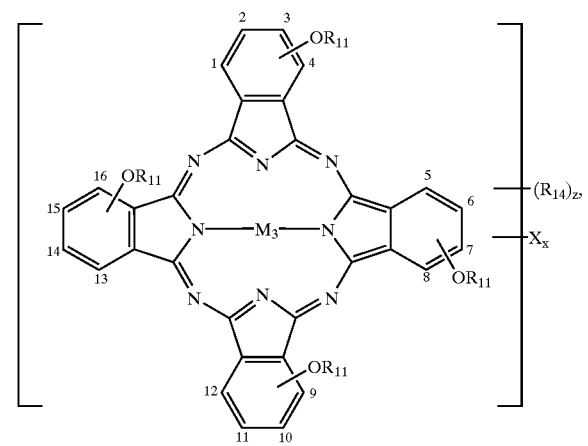

wherein $R_{14}$ may be —CHO, —CH$_2$OH, —COOH, —CH$_2$OC(O)—$C_1-C_4$alkyl or an acetal, and z may be 1 or 2,
wherein —OR$_{11}$, X and $M_3$ each have the same meanings in formulae II and IV and are as defined for claim 8, the mol-% amounts making up 100%, into said recording layer.

8. A process according to claim 7 wherein the optical recording medium is a DVD, a diffractive-optical element or medium for recording a hologram.

9. An optical recording medium, which comprises a metallocenyl-phthalocyanine represented by formula I

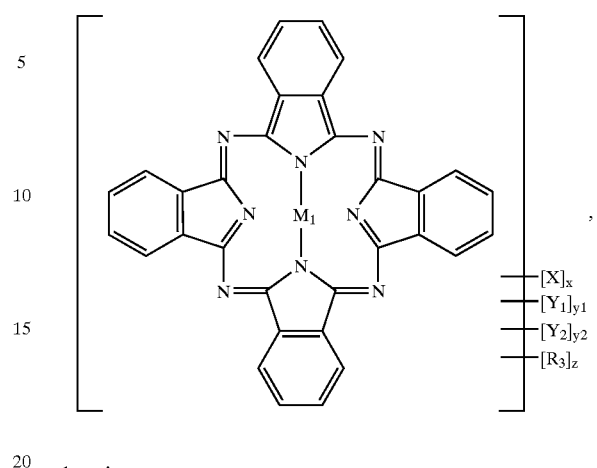

wherein
$M_1$ is a divalent metal, an oxometal group, halogenometal group or hydroxymetal group, or two hydrogen atoms,
X is halogen
$Y_1$ is —OR$_1$, —OOC—R$_2$, —NHR$_1$, —N(R$_1$)R$_2$,
$Y_2$ is —SR$_1$,
$R_3$ is

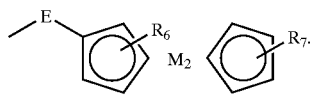

$R_6$ and $R_7$ are each independently of the other hydrogen, halogen, $C_1-C_4$alkyl, $C_1-C_4$alkoxy, amino-$C_1-C_4$alkyl, diarylphosphine, or phosphorus-containing $C_1-C_4$alkyl,
$M_2$ is a transition metal cation,
x may be a rational number from 0 to 8
$y_1$ and $y_2$ may be each independently of the other a rational number from 0 to 6
z may be a number from 1 to 4,
wherein $(x+y_1+y_2+z)$ is $\leq 16$,
and wherein $R_1$ and $R_2$ may be each independently of the other
$C_1-C_{20}$alkyl which is unsubstituted or substituted by halogen, hydroxy, $C_1-C_{20}$alkoxy, $C_1-C_{20}$alkylamino or $C_2-C_{20}$dialkylamino and which may be interrupted by —O—, —S—, —NH— or —NR$_{10}$—, wherein $R_{10}$ may be $C_1-C_6$alkyl,
$C_5-C_{20}$cycloalkyl, $C_2-C_{20}$alkenyl, $C_5-C_{12}$cycloalkenyl, $C_2-C_{20}$alkynyl, $C_6-C_{18}$aryl or $C_7-C_{18}$aralkyl, and wherein one or two ligands may optionally be bound to the divalent metal atom, the oxometal group, halogenometal group or hydroxymetal group, and E is composed of a chain of at least two members selected from the group consisting of —CH$_2$—, —C(=O)—, —CH(C$_1-C_4$alkyl)—, —C(C$_1-C_4$alkyl)$_2$—, —NH—, —S—, —O— and —CH=CH—, and a substrate which is a homo- or copolymeric plastic.

10. An optical recording medium according to claim 9 wherein the metallocenyl-phthalocyanine compound is represented by formula

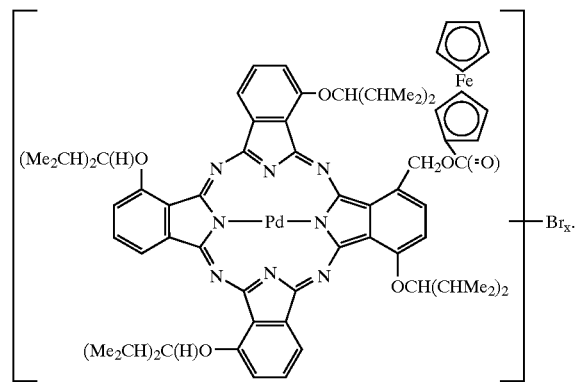

where x=2.6 to 3.0.

11. An optical recording medium according to claim 10 wherein the optical recording medium is a DVD, a diffractive-optical element or medium for recording a hologram.

12. An optical recording medium according to claim 9 wherein the metallocenyl-phthalocyanine compound is represented by formula

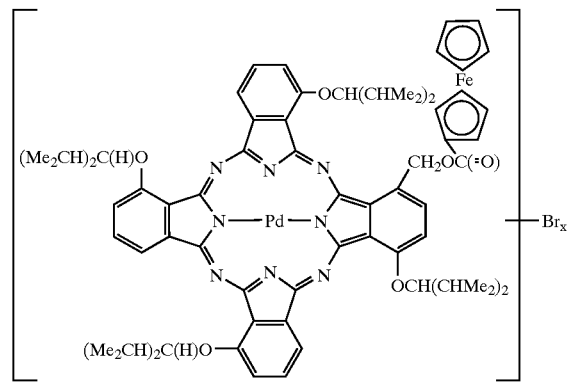

where x = 0 to 0.5.

13. An optical recording medium, which consists essentially of a transparent substrate, a recording layer on that substrate, a reflection layer on the recording layer and, if desired, a final protective layer, the recording layer comprising a metallocenyl-phthalocyanine represented by formula I

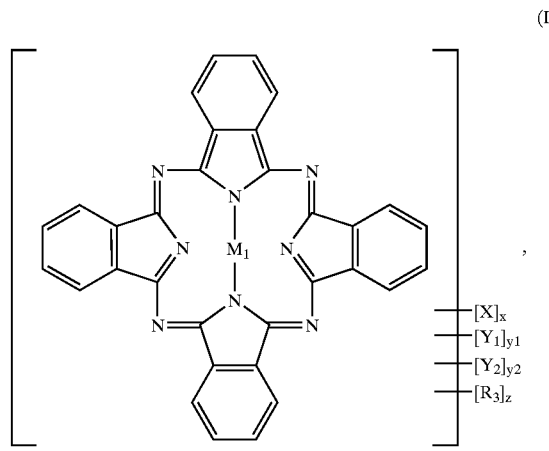

wherein $M_1$ is a divalent metal, an oxometal group, halogenometal group or hydroxymetal group, or two hydrogen atoms, X is halogen $Y_1$ is —$OR_1$, —OOC—$R_2$, —$NHR_1$, —$N(R_1)R_2$, $Y_2$ is $SR_1$, $R_3$ is

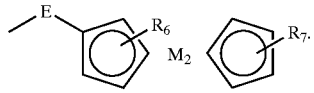

$R_6$ and $R_7$ are each independently of the other hydrogen, halogen, $C_1$–$C_{alkyl}$, $_{C1}$–$C_4$alkoxy, amino-$C_1$–$C_4$alkyl, diarylphosphine, or phosphorus-containing $C_1$–$C_4$alkyl, $M_2$ is a transition metal cation, x may be a rational number from 0 to 8

$y_1$ and $y_2$ may be each independently of the other a rational number from 0 to 6 z may be a number from 1 to 4, wherein ($x+y_1+y_2+z$) is $\leq 16$, and wherein $R_1$ and $R_2$ may be each independently of the other $C_1$–$C_{20}$alkyl which is unsubstituted or substituted by halogen, hydroxy, $C_1$–$C_{alkoxy}$, $_{C1}$–$C_{20}$alkylamino or $C_2$–$C_{20}$dialkylamino and which may be interrupted by —O—, —S—, —NH— or —$NR_{10}$—, wherein $R_{10}$ may be $C_1$–$C_6$alkyl, $C_5$–$C_{20}$cycloalkyl, $C_2$–$C_{20}$alkenyl, $C_5$–$C_{12}$cycloalkenyl, $C_2$–$C_{20}$alkynyl, $C_6$–$C_{18}$aryl or $C_7$–$C_{18}$aralkyl, and wherein one or two ligands may optionally be bound to the divalent metal atom, the oxometal group, halogenometal group or hydroxymetal group, and E is composed of a chain of at least two members selected from the group consisting of —$CH_2$—, —C(=O)—, —CH($C_1$–$C_4$alkyl)—, —C($C_1$–$C_4$alkyl)$_2$—, —NH—, —S—, —O— and —CH=CH—.

14. An optical recording medium according to claim 13 wherein the metallocenyl-phthalocyanine compound is represented by formula

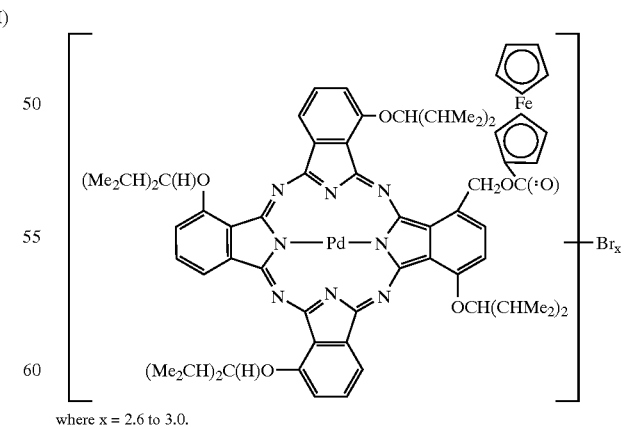

where x = 2.6 to 3.0.

15. An optical recording medium according to claim 13 wherein the metallocenyl-phthalocyanine compound is represented by formula

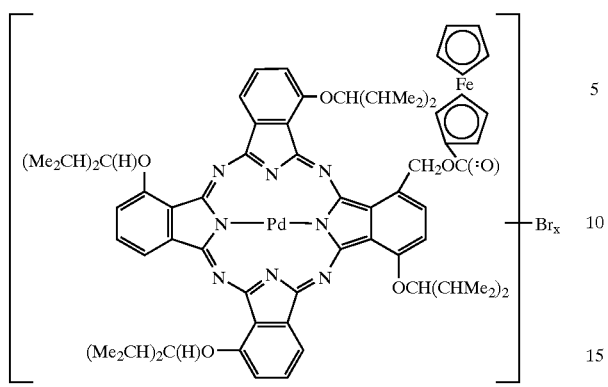
where x = 0 to 0.5.
16. An optical recording medium according to claim 15 wherein the optical recording medium is a DVD, a diffractive-optical element or medium for recording a hologram.
* * * * *